United States Patent
McKinley et al.

(10) Patent No.: US 9,738,591 B2
(45) Date of Patent: Aug. 22, 2017

(54) ANTIMICROBIAL COMPOUNDS

(71) Applicant: Ramiz Boulos, Forrestfield (AU)

(72) Inventors: Allan James McKinley, Woodlands (AU); Thomas V. Riley, East Perth (AU); Nigel Lengkeek, Brighton-Le Sands (AU); Scott Stewart, West Leederville (AU); Ramiz Boulos, Forrestfield (AU)

(73) Assignee: Ramiz Boulos, Forrestfield (AU)

( * ) Notice: Subject to any disclaimer, the term of this patent is extended or adjusted under 35 U.S.C. 154(b) by 0 days.

(21) Appl. No.: 14/592,629

(22) Filed: Jan. 8, 2015

(65) Prior Publication Data
US 2015/0189873 A1   Jul. 9, 2015

Related U.S. Application Data

(62) Division of application No. 13/517,455, filed as application No. PCT/AU2010/001709 on Dec. 21, 2010, now Pat. No. 9,023,892.

(30) Foreign Application Priority Data

Dec. 21, 2009  (AU) ................ 2009906204

(51) Int. Cl.
C07C 309/00    (2006.01)
C07C 69/76     (2006.01)
(Continued)

(52) U.S. Cl.
CPC .............. *C07C 69/76* (2013.01); *A01N 37/10* (2013.01); *A61K 31/194* (2013.01);
(Continued)

(58) Field of Classification Search
CPC ....... C07C 63/66; C07C 63/331; C07C 69/76; C07D 213/24
(Continued)

(56) References Cited

U.S. PATENT DOCUMENTS 3,991,049 A   11/1976   Siegrist et al.
4,618,449 A   10/1986   Roggero et al.
(Continued)

FOREIGN PATENT DOCUMENTS

CN   101016248 A    8/2007
EP      347854 A2   12/1989
(Continued)

OTHER PUBLICATIONS

Gross et al. Angewandte Chemie, International Edition in English, 1995, vol. 34, No. 4, pp. 481-484.*
(Continued)

*Primary Examiner* — Shengjun Wang
(74) *Attorney, Agent, or Firm* — Marshall, Gerstein & Borun LLP

(57) ABSTRACT

A compound for use as an antimicrobial having a formula (A).

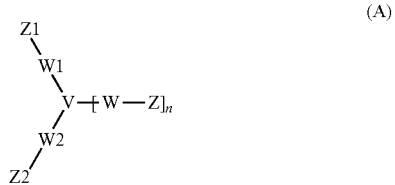

12 Claims, 19 Drawing Sheets

(51) Int. Cl.
  A61K 31/235    (2006.01)
  A61K 31/194    (2006.01)
  A61K 31/444    (2006.01)
  A01N 37/10     (2006.01)
  C07C 63/331    (2006.01)
  C07C 63/66     (2006.01)
(52) U.S. Cl.
  CPC .......... *A61K 31/235* (2013.01); *A61K 31/444* (2013.01); *C07C 63/331* (2013.01); *C07C 63/66* (2013.01)
(58) Field of Classification Search
  USPC ............ 562/488, 489, 480; 560/76; 546/255
  See application file for complete search history.

(56) References Cited

U.S. PATENT DOCUMENTS

| | | | |
|---|---|---|---|
| 4,820,882 | A | 4/1989 | Eckhardt et al. |
| 5,665,500 | A | 9/1997 | Suzuki |
| 5,977,117 | A | 11/1999 | Chan et al. |
| 2004/0014963 | A1 | 1/2004 | Atwood et al. |
| 2010/0012587 | A1 | 1/2010 | Attias et al. |
| 2011/0189090 | A1 | 8/2011 | Wang et al. |
| 2014/0079635 | A1 | 3/2014 | Wang |

FOREIGN PATENT DOCUMENTS

| | | |
|---|---|---|
| EP | 1009042 A2 | 6/2000 |
| IN | 200801176 | 4/2009 |
| JP | 02-229136 | 9/1990 |
| JP | 0 2279767 | 11/1990 |
| JP | 9265194 | 10/1997 |
| JP | 11283748 | 10/1999 |
| JP | 0 3002873 B2 | 1/2000 |
| JP | 0 3006569 B2 | 2/2000 |
| JP | 2000058263 A | 2/2000 |
| JP | 0 3296595 B2 | 7/2002 |
| JP | 2002348530 A | 12/2002 |
| JP | 2005263665 A | 9/2005 |
| JP | 2007219126 A | 8/2007 |
| JP | 2 009235269 A | 10/2009 |
| JP | 2009235269 A | 10/2009 |
| JP | 0 5078261 B2 | 11/2012 |
| JP | 0 5125359 B2 | 1/2013 |
| PL | 0210895 A1 | 6/1980 |
| WO | WO-95/05367 A1 | 2/1995 |
| WO | WO-95/26327 A1 | 10/1995 |
| WO | WO-97/25321 A2 | 7/1997 |
| WO | WO-2007/013459 A1 | 2/2007 |
| WO | WO-2009/138840 A1 | 11/2009 |
| WO | WO-2010/062264 A1 | 6/2010 |
| WO | WO-2013/126898 A1 | 8/2013 |

OTHER PUBLICATIONS

ChemWIKL. The Wittig Reaction, http://chemwiki.ucdavis.edu/?title=Organic_Chemistry/Aldehydes_and_Ketones/Reactivity_of_Aldehydes_%26_Ketones/The_Wittig_Reaction.*
Mekelburger et al. Chemische Berichte, 1993, vol. 126, No. 7, 1713-1721, CAPlus Abstract, AN 1994:106967.*
Sun et al. "Synthesis, Photophysical properties, and photoinduced luminescence switching of trinuclear diimine rhenium(I) tricarbonyl complexes linked by an isomerizable stilbene-like ligand," Organometallics 2002, vol. 21, pp. 39-49.*
Lansky et al. "Highly efficient alkene-alkene and arene-alkene coupling reactions with vicinal dibromides," Synlett, 1990, vol. 7, pp. 405-407.*
Ayer'yanov, Dimension of mesogenic molecules as atomic clusters, Physics of the Solid State, 47(2):378-89 (2005).
Boulos et al., Inspiration from old dyes: Tris(stilbene) compounds as potent gram positive antibacterial agents, Chemistry—A European J., 19:17980-8 (2013).
Chemical Abstract RN 1027582-68-8 (Jun. 12, 2008).
Chemical Abstract RN 134449-01-7 (Jun. 21, 1991).
Chemical Abstract RN 190385-59-3 (Jun. 26, 2007).
Chemical Abstract RN 248278-77-5 (Nov. 22, 1999).
Chemical Abstract RN 264880-96-8 (May 15, 2000).
Chemical Abstract RN 557077-97-1 (Jul. 30, 2003).
Chemical Abstract RN 565209-71-4 (Aug. 12, 2003).
Chemical Abstract RN 868852-79-3 (Nov. 29, 2005).
Chemical Abstract RN 941279-06-7 (Jul. 5, 2007).
Flaherty et al., Polyfluorinated bis-styrylbenzene beta-amyloid plaque binding ligands, J. Med. Chem., 50(20):4986-92 (2007).
International Preliminary Report on Patentability, international application No. PCT/AU2010/001709 (Jun. 26, 2012).
International Search Report and Written Opinion, International application No. PCT/AU2010/001709 (Mar. 25, 2011).
Keller et al., Carbon nanotube formation in situ during cerbonization in shaped bulk solid cobalt nanoparticle compositions, J. Mater. Chem., 14(20):3063-70 (2004).
Muller et al., Chemical behaviour of acetylene complexes. V. Double indenoindene preparation via an unstable platinum (IV) chloride complex with 1,2,4,5-tetraphenylenethynylbenzene, Tetrahedron Lett., 59:5167-70 (1969).
Schramm et al., A QMB-based temperature-modulated ammonia sensor for humid air, Sensors and Actuators, B: Chemical, B67(3): 219-26 (2000).
Agenet et al., Organic Reactions, (Hoboken, NJ, United States) 68:1-302 (2007).—Database Entry Only.
Benshafrut et al., Metal reduction of di- and trisubstituted styrylbenzenes: formation of the highly charged tetra- and hexaanions, *J. Phys. Org. Chem.*, 12(4):333-9 (1999).
Bi et al., Facile synthesis of two-photon absorbing polymers through radical copolymerization, *eXPRESS Polymer Letters*, 1(8):482-7 (2007).
Bi et al., Synthesis and optical properties of symmetric organic molecules and polymers, *Polymer Preprints (American Chemical Society, Division of Polymer Chemistry)* 42(2):441-2 (2001).—Database Entry Only.
Chaitanva et al., Indian Journal of Chemistry, Section A: Inorganic, Bio-inorganic, *Physical, Theoretical & Analytical Chemistry*, 47A(8):1171-80 (2008).—Database Entry Only.
Dmitrieva et al., Polarographic study of styrylbenzenes, Zhurnal Obshchei Khimii, 44(2):352-8 (1974).—Database Entry Only.
Du et al.,Aryene reactions of polyhalobenzenes with alkenyl and alkynyl Grignard reagents, *J. Org. Chem.*, 52(19):4311-4 (1987).—Database Entry Only.
Fiorini-Debuisschert, Controlling molecular organization for the realization of sub-wavelength light sources, *Nonlinear Optics, Quantum Optics*, 40(1-4, Pt. 1):293-305 (2010).—Database Entry Only.
He et al., Synthesis and photophysical properties of linear and hyperbranched conjugated polymer, *Chinese Science Bulletin*, 46(8):636-41 (2001).—Database Entry Only.
Hu, Synthesis, characterization and NLO properties of octupolar molecules, Hong Kong University of Science and Technology, thesis, 349:5422 (2005).—Database Entry Only.
Kononenko et al., Kinetics study of photochemical reactions of 1,3,5-tribinylvenzene derivatives in poly(vinylchloride), *Stsintillyatory i Organicheskie Lyuminofory*, 3:51-6 (1974).—Database Entry Only.
Kovalenko et al., Formation of triaryl derivatives of 1,3,5-trivinylbenzene, Zhurnal Organicheskoi Khimii 7(10): 2149-52 (1971).—Database Entry Only.
Lansky, Highly efficient alkene-alkene and arene-alkene coupling reactions with vicinal dibromides, *Synlett*, (7):405-7 (1990).—Database Entry Only.
Lin et al., Design, Synthesis and photophysical properties of a hyperbranched conjugated polymer, *Thin Solid Films*, 363(1,2):122-5 (2000).—Database Entry Only.
Liu et al., Heck reaction catalyzed by colloids of delaminated Pd-containing layed double hydroxide, *J. Mol. Cat. A: Chem.*, 290(1-2):72-78 (2008).

(56) References Cited

OTHER PUBLICATIONS

Lutskii et al., Electronic vibrational spectra of w-triaryl-substituted 1,3,5-trivinylbenzenes, *Vestnik Khar'kovskogo Politekhnicheskogo Instituta*, 76:3-7 (1973).—Database Entry Only.

Malkes et al. Syntheiss of triaryl-substituede 1,3,5-trivinylbenzenes, *Zhurnal Obshchei Khimii.*, 2(2):297-8 (1966).—Database Entry Only.

Malkes et al., Formation of aryl derivatives of di- and trivinylbenzenes studied by the method of PO-olefination, *Zhurnal Obshchei Khimii.*, 45(7):1481-3 (1975).—Database Entry Only.

Malkes et al., Infrared absorption spectra of triaryl derivatives of 1,3,5-trivinylbenzene, *Zhurnal Prikladnoi Spektroskopii*, 24(3):541 (1976).—Database Entry Only.

Malkes et al., Luminescence and scintillation properties of triaryl-substitued 1,3,5-trivinylbenzene, *Zhurnal Prikladnoi Spektroskopii*, 17(3):538-9 (1972).—Database Entry Only.

Malkes et al., Luminescent defectoscopic compositions based on organic luminophors, *Izvestiya Akademii Nauk SSSR, Seriya Fizicheskaya* 47(7):1419-22 (1983).—Database Entry Only.

Malkes et al., Luminesence and scintillation properties of functional-substituated 1,3,5-tristyrylbenzene derivatives, *Stsintill. Org. Lyuminofory*, 40-6 (1972).—Database Entry Only.

Malkes et al., Luminesence and scintillation properties of triaryl-substituted 1,3,5-trivinyl benzene, *Zhurnal Prikladnoi Spektroskopii*, 11(5):854-8 (1969).—Database Entry Only.

Malkes et al., Synthesis and spectral study of aryl-substituted di- and trivinylbenzenes, *Stsintillyatory Organicheskie Lyuminofory*, 3:42-50 (1974).—Database Entry Only.

Malkes, Luminesence and scintillation properties of w-aryl derivatives of divinyl- and trivinylbenzenes, *Deposited Doc.* SPSTL, 533 Khp-D81, 7 (1981).—Database Entry Only.

Meier et al., Fluoresence of styryl-substituted benzenes, *Chemische Berichte*, 119(5):1716-24 (1986).—Database Entry Only.

Merkushev et al., Photochemical synthesis of polynuclear hydrocarbons. IV. Unexpected photochemical dehydrocyclization of 1,3,5-tristyrylbenzene, V. I. *Zhurnal Organicheskoi Khimii*, 19(11):2387-9 (1983).—Database Entry Only.

Mueller et al., Chemical behavior of acetylene complexes. V. Double indenoindene preparation via an unstable platinum(IV) chloride complex with 1,2,4,5-tetraphenylethynylbenzene, *Tetrahedron Letters*, (59):5167-70 (1969).—Database Entry Only.

Prukala, A novel approach to stilbenoid dendrimer core synthesis, *W Synlett*, (19):3026-30 (2008).—Database Entry Only.

Rios, Cerealbolinic acid. A new athraquinone pigment isolated from Ceroplastes albokineatus, *Tetrahedron*, 22(4):1507-12 (1966).—Database Entry Only.

Siegrist et al., Anil synthesis. III. Preparation of styryl derivatives from methyl-substituted carbocyclic aromatic compounds, *Helvetica Chimica. Acta.*, 52(8), 2521-54 (1969).—Database Entry Only.

Simkin, Interpretation of the electronic spectra of some w-aryl-substituted vinylbenzenes, *Izvestiya Severo-Kavkazskogo Nauchnogo Tsentra Vysshei Shkoly, Estestvennye Nauki*, (4):98-9 (1977).—Database Entry Only.

Tobe et al., Synthesis of polynuclear cyclophanes, *Science of Synthesis*, 45b:1311-48 (2010).—Database Entry Only.

Uda et al., 1 3 5-Tristyrylbenzene dendrimers: a novel model system to explore oxygen quenching in a highly organized environment, *Organic & Biomolecular Chemistry*, 1(10):1635-7 (2003).

Winter et al., Photochemistry of 1,3,5-tristyrylbenzene, *Chemische Berichte*, 117(7):2452-63 (1984).—Database Entry Only.

Yur'ev et al., Simple way to a new cyclophane, *Angewandte Chemie*, 93(3):285- 6 (1981).—Database Entry Only.

* cited by examiner

TSB065　　　　　　　　TSB066

TSB067

TSB068

ANTIMICROBIAL COMPOUNDS

FIELD OF THE INVENTION

The present invention relates to novel aryl compounds. More particularly the present invention relates to novel aryl compounds and their use as antimicrobials to treat bacterial infections or diseases.

BACKGROUND ART

Compounds with antimicrobial properties have attracted great interest in recent times as a result of an increase in the prevalence of infections caused by Gram-positive bacteria, resulting in serious or fatal diseases. Furthermore, the regular use of broad spectrum antibiotic formulas has led to the increased occurrence of bacterial strains resistant to some antimicrobial formulations.

Novel antimicrobial compounds have the potential to be highly effective against these types of treatment-resistant bacteria. The pathogens, having not previously been exposed to the antimicrobial formulation, may have little to no resistance to the treatment.

DISCLOSURE OF THE INVENTION

General

Those skilled in the art will appreciate that the invention described herein is susceptible to variations and modifications other than those specifically described. It is to be understood that the invention includes all such variation and modifications. The invention also includes all of the steps, features, compositions and compounds referred to or indicated in the specification, individually or collectively and any and all combinations or any two or more of the steps or features.

The present invention is not to be limited in scope by the specific embodiments described herein, which are intended for the purpose of exemplification only. Functionally equivalent products, compositions and methods are clearly within the scope of the invention as described herein.

The entire disclosures of all publications (including patents, patent applications, journal articles, laboratory manuals, books, or other documents) cited herein are hereby incorporated by reference, which means that it should be read and considered by the reader as part of this text. That the document, reference, patent application or patent cited in this text is not repeated in this text is merely for reasons of conciseness. No admission is made that any of the references constitute prior art or are part of the common general knowledge of those working in the field to which this invention relates.

Throughout this specification, unless the context requires otherwise, the term antimicrobial is understood to include compounds with antibacterial properties.

Throughout this specification, unless the context requires otherwise, the word "comprise", or variations such as "comprises" or "comprising", will be understood to imply the inclusion of a stated integer or group of integers but not the exclusion of any other integer or group of integers.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

Use of Compounds

In one form, the present invention provides for the use of a compound of Formula A, or a pharmaceutically acceptable salt thereof in the manufacture of a medicament for the therapeutic treatment of bacterial infection or disease in a subject in need thereof.

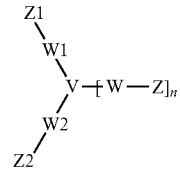

(Formula A)

Where;
W is a linking unit and Z is a peripheral unit. V, linking unit W and peripheral unit Z are all linked by co-valent bonds;
n=1, 2, 3, or 4.
V=a six membered aromatic ring.
The, or each W may be independently selected from:
i. $C_{2-4}$ alkyl groups;
ii. $C_{2-4}$ substituted alkyl groups;
iii. $C_2$ E-alkene, with V and Z in the 1 and 2 positions;
iv. $C_2$ Z-alkene, with V and Z in the 1 and 2 positions;
v. $C_2$-alkyne;
The, or each Z may be selected from any one or more of:

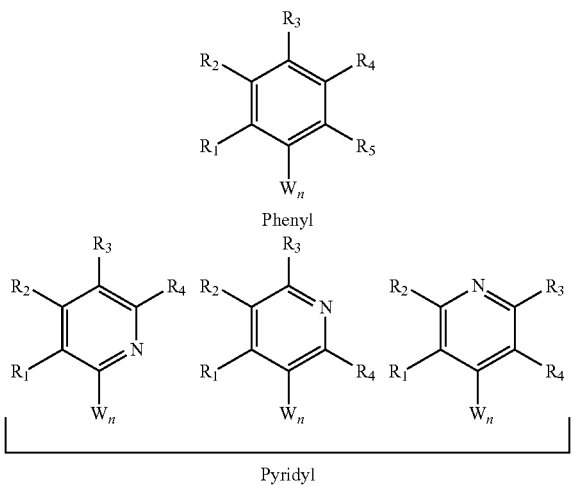

Phenyl

Pyridyl $R_n$ may be independently selected from any one or more of i-xxxvii, with at least one R group being independently selected from any one of ii-xxxvii:
i. —H,
ii. -Halo,
iii. $C_{1-8}$ alkyl,
iv. $C_{1-8}$ heteroalkyl,
   a) Carboxylic acids and related derivatives independently selected from:
   b) Carboxylic acid,

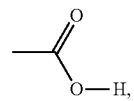

c) Thiocarboxylic acid,

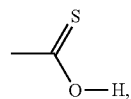

d) Esters,

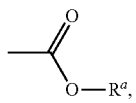

e) Thioester,

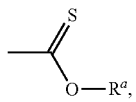

f) Dithioester,

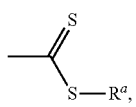

v. Amide derivatives of carboxylic acids independently selected from:
a) Amide,

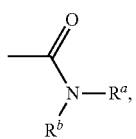

b) Thioamide,

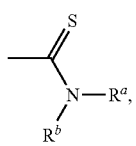

vi. Aldehydes, ketones and their derivatives independently selected from:
a) Aldehyde,

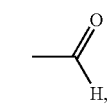

b) Thial,

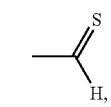

Ketones,

d) Thioketones,

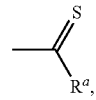

e) Acetals,

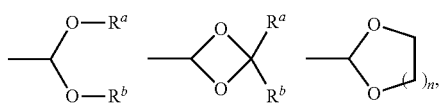

f) Dithioacetals,

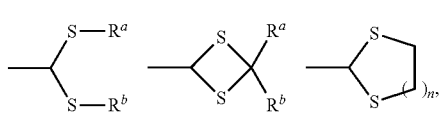

vii. Amines, alkyl amines and their derivatives independently selected from:
a) Amines,

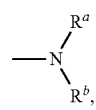

b) Amides,

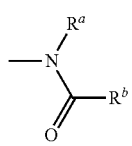

c) Thioamide,

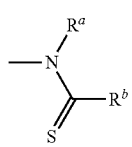

d) Ammonium salts,

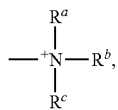

e) Alkyl amines,

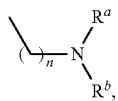

where n=1-3
f) Alkyl amides,

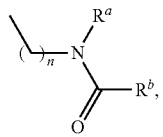

where n=1-3
g) Alkyl thioamides,

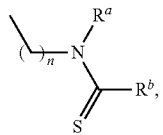

where n=1-3
h) Alkyl ammonium salts,

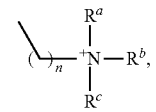

where n=1-3,
i) Imines,

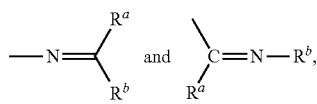

j) Guanidines,

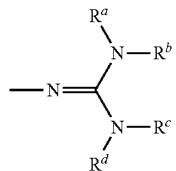

k) Amidine,

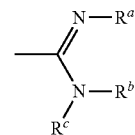

viii. Nitrile (cyano), —C≡N,
ix. Isonitrile,

x. Cyanate, —O—C≡N,
xi. Isocyanate, —N═C═O,
xii. Thiocyanate, —S—C≡N,
xiii. Isothiocyanate, —N═C═S,
xiv. Azo, —N═NH,
xv. Nitro,

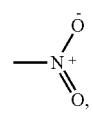

xvi. Nitrite, —O—N═O,
xvii. Nitriso, —N═O,
xviii. N-terminal peptide sequences,

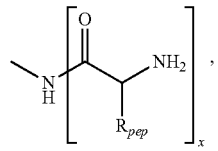

where x=1-3 and $R^{pep}$ is any group resulting in the formation of an amino acid.
xix. C-terminal peptide sequences,

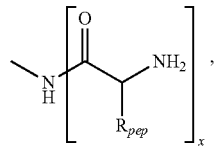

where x=1-3 and $R^{pep}$ is any group resulting in the formation of an amino acid.
xx. Phosphorus based substituents, where the phosphorus atom is in either the 3+ or 5+ oxidation state, independently selected from:
a) Phosphines,

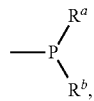

b) Phosphine oxides,
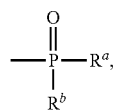
c) Phosphites,
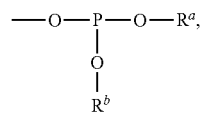
d) Phosphates,
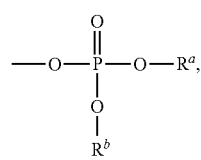
e) Phosphinites,
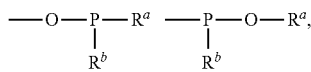
f) Phosphinates,
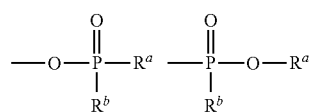
g) Phosphinites,
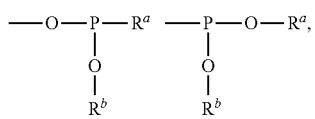
h) Phosphonates,
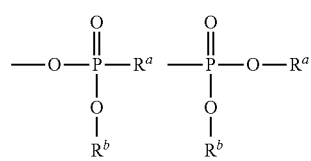
xxi. sulfur based substituents,
  a) Sulfate,
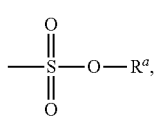
b) Sulfone
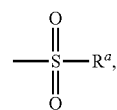
c) Sulfoxide,
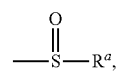
d) Sulfinic acids,
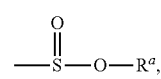
e) Sulfimines,
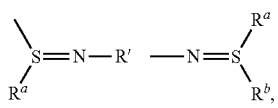
f) Sulfonamides,
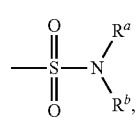
xxii. Boron based substituents,
  a) Boronic acids,
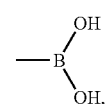
b) Boronic esters,
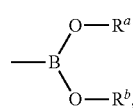
xxiii. Semicarbazones,
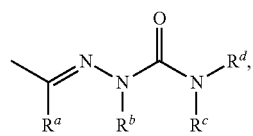

xxiv. Thiosemicarbazones,

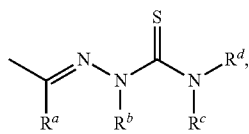

xxv. Cyanimide,

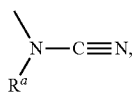

xxvi. Hydrazone,

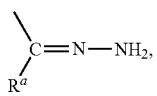

xxvii. Oxime,

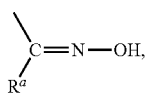

xxviii. Nitroamine,

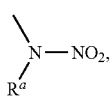

xxix. Nitronate,

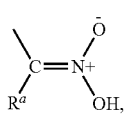

xxx. Nitrone,

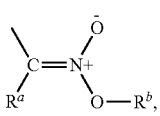

xxxi. Carbonates,

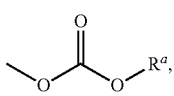

xxxii. Carbamates,

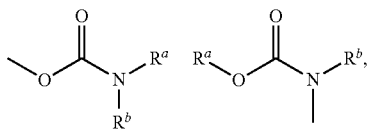

xxxiii. Dithiocarbamates,

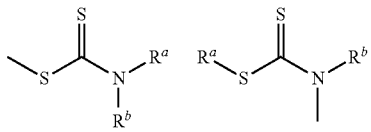

xxxiv. A 5- or 6-membered saturated heterocyclic ring containing 1 to 3 heteroatoms chosen independently from nitrogen, sulfur and oxygen.

xxxv. A 5- or 6-membered saturated heteroaromatic ring containing 1 to 5 heteroatoms chosen independently from nitrogen, sulfur and oxygen.

xxxvi. A 5-membered unsaturated heterocyclic ring containing, one or two double bonds and containing 1 to 5 heteroatoms chosen independently from nitrogen, sulphur and oxygen.

xxxvii. A 6 membered ring containing 1 to 3 double bonds and containing) to 5 heteroatoms chosen independently from nitrogen, sulfur and oxygen dependant on ring size.

The present invention further provides for the use of a compound of Formula B:

(Formula B)

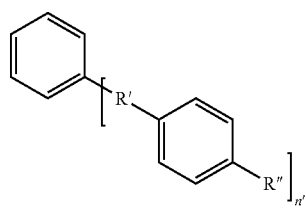

or a pharmaceutically acceptable salt thereof in the manufacture of a medicament for the therapeutic treatment of bacterial infection or disease in a subject in need thereof, wherein:

n'=2, 3 or 4

R' comprises any one of $C_2$-alkyl, $C_2$-alkene or $C_2$-alkyne; and

R" is independently selected from $NH_2$, $CH_3$, OH, —$COCH_3$, —$OC(CH_3)_3$, $OCH_3$, $OCH_2CH_3$, $OCH(CH_3)_2$, —$CONH_2$, COOH, $COOCH_3$, or $COOCH_2CH_3$ In a preferred form, the present invention provides for the use of a compound of Formula B:

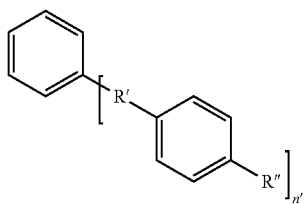

(Formula B)

or a pharmaceutically acceptable salt thereof in the manufacture of a medicament for the therapeutic treatment of bacterial infection or disease in a subject, in need thereof wherein:

n'=2, 3 or 4

R'=$C_2$-alkyl or $C_2$-alkene

R" is independently selected from $COOCH_3$, $COOCH_2CH_3$ or COOH

In a further preferred form, the invention provides for the use of a compound of Formula C:

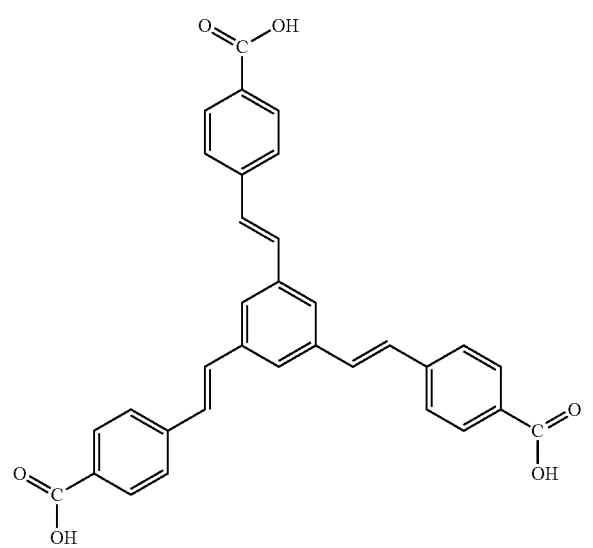

(Formula C)

or a pharmaceutically acceptable salt thereof in the manufacture of a medicament for the therapeutic treatment of bacterial infection or disease in a subject in need thereof.

The compound of Formula C is also known as NAL135B, 135B and TSB007 (see FIG. 7).

In an alternative aspect, the compound provided for the use of a compound selected from the following list of analogues of formula C: TSB049, TSB063, TSB037, TSB041, TSB019, TSB023, TSB025, TSB065, TCT003, TSB001, TSB009, TSB053, TAB001, TCB001, TCB003 (see FIGS. 8 to 12 for structure information). More preferably, the compound is TSB065 or TCB001.

The use of a compound of any one of Formulas A, B or C, or analogues thereof, or pharmaceutically acceptable salts thereof in the manufacture of a medicament for the therapeutic treatment of bacterial infection or disease in a subject in need thereof, wherein the bacterial infection or disease results from Gram-positive bacteria.

Method of Treatment

The compounds of the present invention have antimicrobial activity, and thus are useful for treatment of bacterial infections. Thus, the present invention also provides a method of treating a bacterial infection in a subject comprising the step of administering to the subject an effective amount of a compound of Formula A and variants described herein.

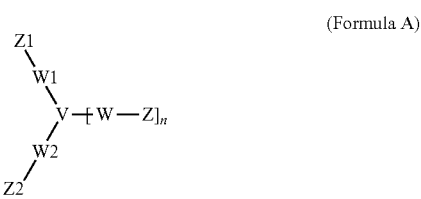

(Formula A)

The present invention further provides a method of treating a bacterial infection in a subject comprising the step of administering to the subject an effective amount of a compound of Formula B:

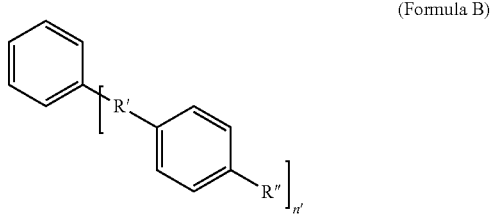

(Formula B)

Wherein:

n'=2, 3 or 4

R' comprises any one of $C_2$-alkyl, $C_2$-alkene or $C_2$-alkyne; and

R" is independently selected from $NH_2$, $CH_3$, OH, —$COCH_3$, —$OC(CH_3)_3$, $OCH_3$, $OCH_2CH_3$, $OCH(CH_3)_2$, —$CONH_2$, COOH, $COOCH_3$, or $COOCH_2CH_3$.

In a preferred form the present invention provides a method of treating a bacterial infection in a subject comprising the step of administering to the subject an effective amount of a compound of Formula B wherein:

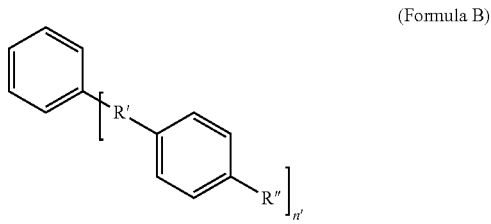

(Formula B)

n'=2, 3 or 4

R'=c2-alkyl o $C_2$-alkene

R" is independently selected from $COOCH_3$, $COOCH_2CH_3$ or COOH

In a further preferred form, the present invention provides a method of treating a bacterial infection in a subject comprising the step of administering to the subject an effective amount of a compound of Formula C:

(Formula C)

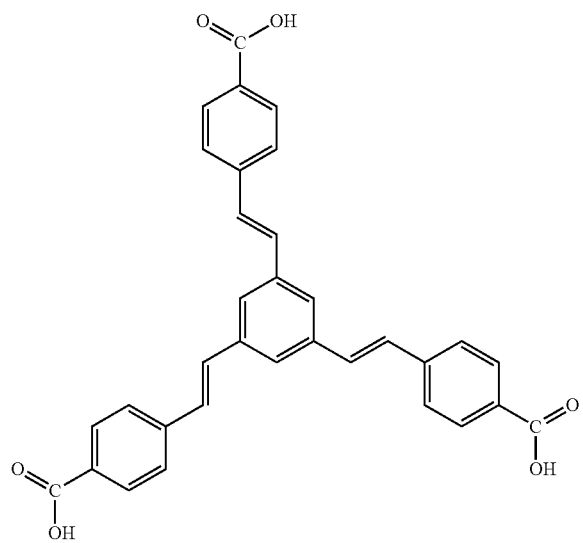 [SMILES: O=C(O)c1ccc(/C=C/c2cc(/C=C/c3ccc(C(=O)O)cc3)cc(/C=C/c3ccc(C(=O)O)cc3)c2)cc1]

In an alternative aspect, the present invention provides a method of treating a bacterial infection in a subject comprising the step of administering to the subject an effective amount of a compound selected from the following list of analogues of formula C: TSB049, TSB063, TSB037, TSB041, TSB019, TSB023, TSB025, TSB065, TCT003, TSB001, TSB009, TSB053, TAB001, TCB001, TCB003 (see FIGS. 8 to 12 for structure information). More preferably, the compound is TSB065 or TCB001.

The compounds of the present invention are understood to be effective against both Gram positive bacteria and Gram negative bacteria.

Examples of Gram-negative bacteria which the compounds of the present invention may preferably be used against include: *Aeromonas hydrophila, Citrobacter freundii, Escherichia coli, Klebsiella edwardsii, Proteus mirabilis, Salmonella enterica* subsp. *enterica* serovar *Typhimurium, Moraxella catarrhalis, Shigella flexneri, Stenotrophomonas maltophilia, Vibrio cholerae* (non-toxigenic) and *Yersinia enterocolitica*.

The compounds of the present invention are understood to be most effective against Gram-positive bacteria. Examples of Gram-positive bacteria which the compounds of the present invention may preferably be used against include: *Bacillus cereus, Bacillus subtilise, Clostridium difficile, Enterococcus faecalis, Enterococcus faecium, Listeria monocytogenes, Micrococcus luteus, Staphylococcus aureus, Staphylococcus aureus* (methicillin resistant), *Staphylococcus epidermidis, Staphylococcus xylosus, Streptococcus pneumonia,* and *Streptococcus pyogenes*.

The compounds of the present invention are understood to be particularly effective against methicillin-resistant *Staphylococcus aureus* (MRSA) and *Clostridium difficile*.

Compositions

The compounds of the present invention may be formulated into compositions for administration.

Thus, the present invention also provides a composition comprising a therapeutically-effective amount of a compound of Formula A and variants described herein, and a pharmaceutically acceptable carrier or diluent.

(Formula A)

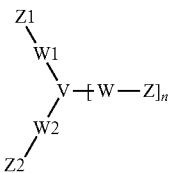

The present invention also provides a composition comprising a therapeutically-effective amount of a compound having a Formula B and a pharmaceutically acceptable carrier or diluents:

(Formula B)

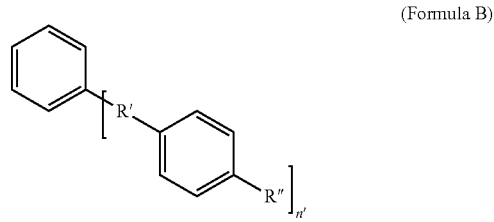

n=2, 3 or 4

R' comprises any one of $C_2$-alkyl, $C_2$-alkene or $C_2$-alkyne; and

R" is independently selected from $NH_2$, $CH_3$, OH, —$COCH_3$, —$OC(CH_3)_3$, $OCH_3$, $OCH_2CH_3$, $OCH(CH_3)_2$, —$CONH_2$, COOH, $COOCH_3$, or $COOCH_2CH_3$.

In a preferred form, the present invention provides a composition comprising a therapeutically-effective amount of a compound having a Formula B and a pharmaceutically acceptable carrier or diluents (Formula B)

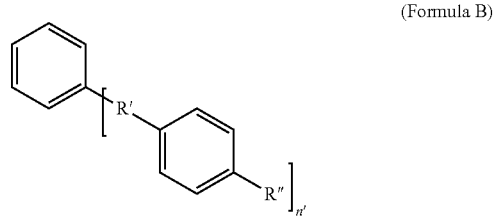

wherein:

n=2, 3 or 4

R'=$c_2$-alkyl o $C_2$-alkene

R" is independently selected from $COOCH_3$, $COOCH_2CH_3$ or COOH.

The present invention also provides a composition comprising a therapeutically-effective amount of a compound having a Formula C and a pharmaceutically acceptable carrier or diluent.

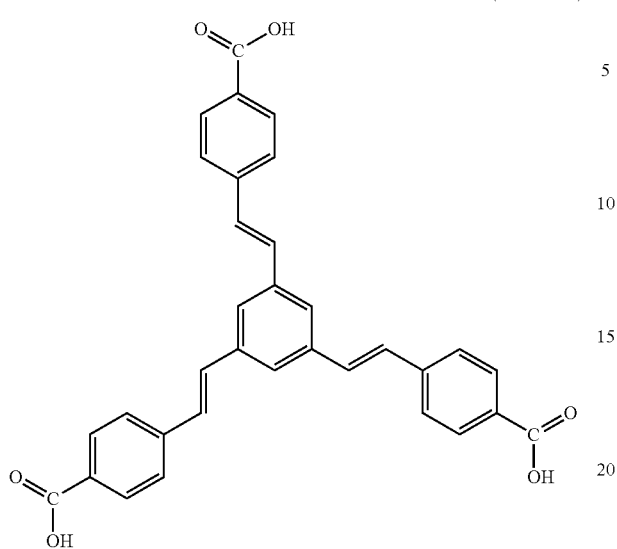

(Formula C)

In an alternative aspect of the present invention, there is provided a composition comprising a therapeutically-effective amount of a compound selected from the following list of analogues of compound C: TSB049, TSB063, TSB037, TSB041, TSB019, TSB023, TSB025, TSB065, TCT003, TSB001, TSB009, TSB053, TAB001, TCB001, TCB003 (see FIGS. 8 to 12 for structure information) and a pharmaceutically acceptable carrier or diluent. More preferably, the compound is TSB065 or TCB001.

With respect to use, methods of treatment and compositions comprising the compounds having a Formula A, B or C, or analogues thereof and variants described herein:—

V is preferably, a phenyl or a pyridal ring.

Where V is a phenyl ring and:
i. n=3, the W—Z group may be substituted at positions 1, 2, and 3; or 1, 2, and 4; or 1, 3 and 5, with $A^1$, $A^2$ and $A^3$ occupying remaining positions on the ring:

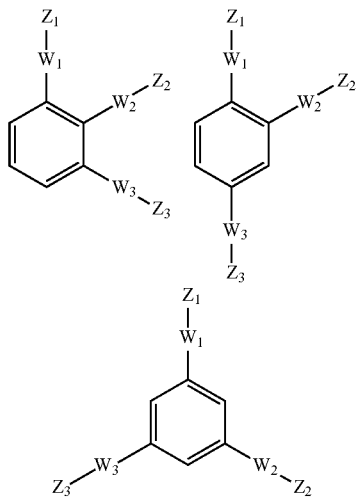

ii. n=4, W—Z may be substituted at positions 1, 2, 3 and 4; 1, 2, 3 and 5; 1, 2, 4 and 5 with $A^1$ and $A^2$ occupying remaining positions on the ring:

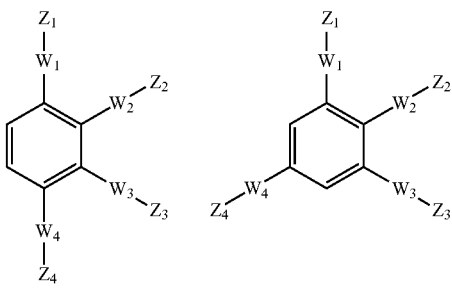

iii. n=5, W—Z may be substituted at positions 1, 2, 3, 4 and 5 with $A^1$ occupying the remaining position on the ring:

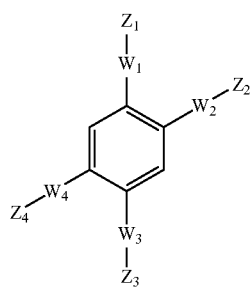

iv. n=6, W—Z is substituted into each of positions 1, 2, 3, 4, 5 and 6.

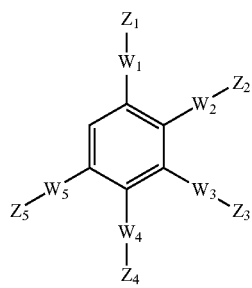

Where V is a pyridal ring, and:
i. n=3, W—Z may be substituted into positions 2, 3, and 4; or 2, 3, and 5; or 2, 3, and 6; or 2, 5, and 6; or 2, 4 and 6; or 3, 4, and 5, with $A^1$ and $A^2$ occupying the remaining positions on the pyridal ring, and where the pyridal nitrogen (N) occupies position 1.

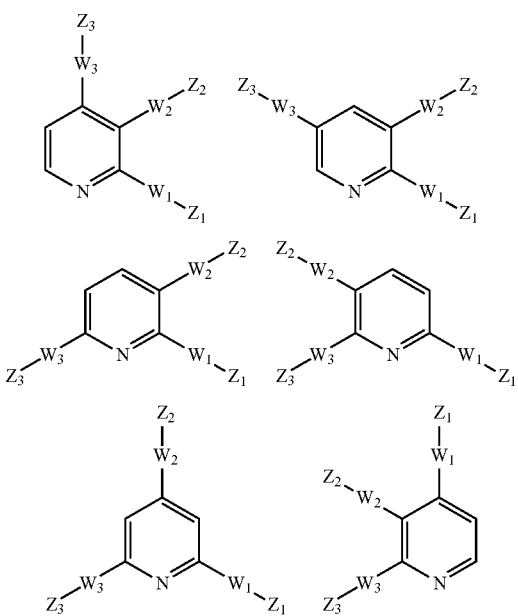

ii. n=4, W—Z may be substituted into positions, 2, 3, 4, and 5; or 2, 3, 5, and 6; with $A^1$ occupying the remaining position on the pyridal ring, and where the pyridal nitrogen (N) occupies position 1.

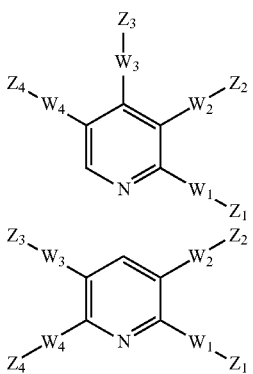

iii. n=5, W—Z may be substituted into positions, 2, 3, 4, 5 and 6; and where the pyridal nitrogen (N) occupies position 1.

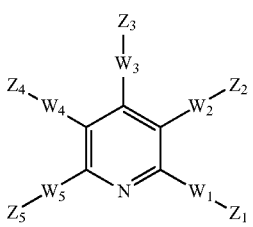

Where the, or each W is in the form of a $C_2$ E-alkene, with V and Z in positions 1 and 2, positions 3 and 4 are each preferably independently substituted with a hydrogen or $C_{1-4}$ alkyl.

Where the, or each W is in the form of a $C_2$ Z-alkene, with V and Z in positions 1 and 2, positions 3 and 4 are each preferably independently substituted with a hydrogen or $C_{1-4}$ alkyl.

Where $R_n$ is a carboxylic acid; the carboxylic acid is preferably in the form of —$COOR^a$.

More preferably, $R^a$ is any one of hydrogen, alkyl ($C_{1-4}$).

Where $R_n$ is an amide derivative of a carboxylic acid, $R^a$ and $R^b$ are independently selected from hydrogen or alkyl ($C_{1-4}$).

Where $R_n$ is an aldehyde, ketone, or a derivative thereof, $R^a$ and $R^b$ are independently selected from hydrogen or alkyl ($C_{1-4}$).

Where $R_n$ is an amine, alkyl amine or a derivative thereof, $R^a$, $R^b$, and $R^c$ are independently selected from hydrogen or alkyl ($C_{1-4}$).

Where $R_n$ is a saturated 5 or 6 membered heterocyclic ring, the heterocycle is preferably any one of piperidinyl, morpholinyl, thiomorpholinyl, thiazolidinyl, isothiazolidinyl, oxazolidinyl, isooxazolidinyl, pyrrolidinyl, imidazolidinyl, piperazinyl, tetrahydrofuranyl, dioxaanyl, dithanyl, and pyrazolidinyl.

The saturated heterocyclic ring may be unsubstituted. Alternatively, the saturated heterocyclic ring may be substituted with 1 to 3 substituents independently selected from:
1. Halogen, independently selected from Br, I, Cl, F
2. Alkyl, independently selected from methyl, ethyl, propyl or butyl Where $R_n$ is a 5 or 6 membered heteroaromatic ring, the heteroaromatic is preferably any one of thienyl, pyridyl, imidazolyl, pyrrolyl, pyrazolyl, thiazolyl, isothiazolyl, oxazolyl, isooxazolyl, pyrazinyl, pyrimidinyl, triazolyl, tetrazolyl, furanyl, triazinyl, and pyridazinyl.

The heteroaromatic ring may be unsubstituted. Alternatively, the heteroaromatic ring may be substituted with 1 to 5 substituents independently selected from:
1. Halogen, independently selected from Br, I, Cl, F
2. Alkyl, independently selected from methyl, ethyl, propyl or butyl Where $R_n$ is an unsaturated 5 or 6 membered heterocyclic ring, the heterocycle is preferably any one of oxolanyl, imidazolinyl, pyrazolinyl, thiazolidinyl, oxazolininyl, dithiolanyl, and dioxolanyl.

More preferably, the unsaturated heterocyclic ring is not an aromatic.

The unsaturated heterocyclic ring may be unsubstituted. Alternatively, the unsaturated heterocyclic ring may be substituted with 1 to 5 substitutents independently selected from:
1. Halogen, independently selected from Br, I, Cl, F
2. Alkyl, independently selected from methyl, ethyl, propyl or butyl.

R' is preferably in the form of any one of $C_2$-alkyl o $C_2$-alkene, and R" is independently selected from $COOCH_3$, $COOCH_2CH_3$ or $COOH$.

Preferably, where n'=2, R'—$C_6H_4$—R", is substituted at positions 1 and 3.

Preferably, where n'=3, R'—$C_6H_4$—R", is substituted at positions 1, 3 and 5; or 1, 2 and 4.

Preferably, where n'=3, R'—$C_6H_4$—R", is substituted at positions 1, 2, 4 and 5.

$R^{pep}$ preferably has a peptide comprised of one or more α-amino acids, independently selected from alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine.

The present invention provides use of a compound of Formulas A, B or C, or analogues thereof, or pharmaceutically acceptable salts thereof in the manufacture of a medicament for the therapeutic treatment of bacterial infection or disease in a subject in need thereof, wherein the bacterial infection or disease results from Gram-positive bacteria.

The precise composition of the present invention will vary according to a wide range of commercial and scientific criteria. Methods for the preparation of pharmaceutical compositions comprising one or more active ingredients are generally known in the art. Such compositions will generally be formulated for the mode of delivery that is to be used and will usually include one or more pharmaceutically acceptable carriers.

Generally, examples of suitable carriers, excipient and diluents include, without limitation, water, saline, ethanol, dextrose, glycerol, lactose, dextrose, sucrose, sorbitol, mannitol, starches, gum acacia, calcium phosphates, alginate, tragacanth, gelatine, calcium silicate, microcrystalline cellulose, polyvinylpyrrolidone, cellulose, water syrup, methyl cellulose, methyl and propylhydroxybenzoates, talc magnesium stearate and mineral oil or combinations thereof. The formulations can additionally include lubricating agents, pH buffering agents, wetting agents, emulsifying and suspending agents, preserving agents, sweetening agents or flavouring agents.

(a) Topicals

The pharmaceutical composition may be adapted for topical application. In this regard, various topical delivery systems may be appropriate for administering the compositions of the present invention depending up on the preferred treatment regimen. Topical formulations may be produced by dissolving or combining the compound of the present invention in an aqueous or nonaqueous carrier. In general, any liquid, cream, or gel or similar substance that does not appreciably react with the compound or any other of the active ingredients that may be introduced into the composition and which is non-irritating is suitable. Appropriate non-sprayable viscous, semi-solid or solid forms can also be employed that include a carrier compatible with topical application and have dynamic viscosity preferably greater than water.

Suitable formulations are well known to those skilled in the art and include, but are not limited to, solutions, suspensions, emulsions, creams, gels, ointments, powders, liniments, salves, aerosols, transdermal patches, etc, which are, if desired, sterilised or mixed with auxiliary agents, e.g. preservatives, stabilisers, emulsifiers, wetting agents, fragrances, colouring agents, odour controllers, thickeners such as natural gums, etc. Particularly preferred topical formulations include ointments, creams or gels.

Ointments generally are prepared using either (1) an oleaginous base, i.e., one consisting of fixed oils or hydrocarbons, such as white petroleum or mineral oil, or (2) an absorbent base, i.e., one consisting of an anhydrous substance or substances which can absorb water, for example anhydrous lanolin. Customarily, following formation of the base, whether oleaginous or absorbent, the active ingredient is added to an amount affording the desired concentration.

Creams are oil/water emulsions. They consist of an oil phase (internal phase), comprising typically fixed oils, hydrocarbons and the like, waxes, petroleum, mineral oil and the like and an aqueous phase (continuous phase), comprising water and any water-soluble substances, such as added salts. The two phases are stabilised by use of an emulsifying agent, for example, a surface active agent, such as sodium lauryl sulfite; hydrophilic colloids, such as acacia colloidal clays, veegum and the like. Upon formation of the emulsion, the compound can be added in an amount to achieve the desired concentration.

Gels comprise a base selected from an oleaginous base, water, or an emulsion-suspension base. To the base is added a gelling agent that forms a matrix in the base, increasing its viscosity. Examples of gelling agents are hydroxypropyl cellulose, acrylic acid polymers and the like. Customarily, the compound is added to the formulation at the desired concentration at a point preceding addition of the gelling agent.

The amount of compound incorporated into a topical formulation is not critical; the concentration should be within a range sufficient to permit ready application of the formulation such that an effective amount of the compound is delivered.

(b) Oral Formulations

The pharmaceutical composition may be adapted for oral delivery. In this regard, the compound can be administered as an oral preparation adapted in such a manner that facilitates delivery of a therapeutically effective concentration of the compound.

The effective dosages of the compound, when administered orally, must take into consideration the diluent, preferably water. The composition preferably, contains 0.05% to about 100% by weight active ingredient and more preferably about 10% to about 80% by weight. When the compositions are ingested, desirably they are taken on an empty stomach.

Contemplated for use herein are oral solid dosage forms including tablets, capsules, pills, troches or lozenges, cachets or pellets. Also, liposomal or proteinoid encapsulation may be used to formulate the present compositions. Liposomal encapsulation may be used and the liposomes may be derivatised with various polymers. In general, the formulation will include the compound and inert ingredients that allow for protection against the stomach environment and release of the biologically active material in the intestine.

The location of release may be the stomach, the small intestine (the duodenum, the jejunem, or the ileum), or the large intestine. One skilled in the art has available formulations that will not dissolve in the stomach, yet will release the material in the duodenum or elsewhere in the intestine. Preferably, the release will avoid the deleterious effects of the stomach environment, either by protection of the composition or by release of the compound beyond the stomach environment, such as in the intestine.

To ensure full, gastric resistance, a coating impermeable to at least pH 5.0 may be used. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S and Shellac. These coatings may be used as mixed films.

A coating or mixture of coatings that are not intended for protection against the stomach can also be used on tablets. This can include sugar coatings, or coatings that make the tablet easier to swallow. Capsules may consist of a hard shell (such as gelatine) for delivery of dry therapeutic i.e. powder; for liquid forms, a soft gelatine shell may be used. The shell material of cachets could be thick starch or other edible paper. For pills, lozenges, moulded tablets or tablet triturates, moist massing techniques can be used.

One may dilute or increase the volume of the composition with an inert material. These diluents could include carbohydrates, especially mannitol, alpha-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the compound into a solid dosage form. Materials used as disintegrants include but are not limited to starch including the commercial disintegrant based on starch, Explotab. Sodium starch glycolate, Amberlite, sodium carboxymethylcellulose, ultramylopectin, sodium alginate, gelatine, orange peel, acid carboxymethyl cellulose, natural sponge and bentonite may all be used. Another form of the disintegrants is insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the composition together to form a hard tablet and include materials from natural products such as acacia, tragacanth, starch and gelatine. Others include methylcellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the compound.

An antifrictional agent may be included in the formulation to prevent sticking during the formulation process. Lubricants may be used as a layer between the compound and the die wall and these can include but are not limited to: stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights and Carbowax 4000 and 6000.

Glidants that might improve the flow properties of the composition during formulation and to aid rearrangement during compression might be added. The glidants may include starch, talc, pyrogenic silica and hydrated silicoaluminate.

To aid dissolution of the compound, a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation either alone or as a mixture in different ratios.

Controlled release formulations may be desirable. The compounds can be incorporated into an inert matrix that permits release by either diffusion or leaching mechanisms i.e., gums. Slowly degenerating matrices may also be incorporated into the formulation. Another form of a controlled release formulation is by a method based on the Oros therapeutic system (Alza Corp.), i.e. the composition is enclosed in a semipermeable membrane which allows water to enter and push the composition out through a single small opening due to osmotic effects. Some enteric coatings also have a delayed release effect.

A mix of materials might be used to provide the optimum film coating. Film coating may be carried out in a pan coater or in a fluidised bed or by compression coating.

The compound can be included in the formulation as fine multiparticulates in the form of granules or pellets of particle size about 1 mm. The formulation of the material for capsule administration could also be as a powder, lightly compressed plugs or even as tablets. The compound could be prepared by compression.

(c) Injectable Formulations

The compound can also be formulated for parenteral delivery. Pharmaceutical forms suitable for injectable use include: sterile aqueous solutions (where water-soluble) or dispersions and sterile powders for the extemporaneous preparation of sterile injectable solutions or dispersion. Alternatively, the compounds of the invention may be encapsulated in liposomes and delivered in injectable solutions to assist their transport across cell membrane. The solution may be a solvent or dispersion medium containing, for example, water, ethanol, polyol (for example, glycerol, propylene glycol and liquid polyethylene glycol and the like), suitable mixtures thereof and vegetable oils. Proper fluidity may be maintained, for example, by the use of a coating such as lecithin, by the maintenance of the required particle size in the case of dispersion and by the use of surfactants. Prolonged absorption of the injectable compositions can be brought about by the use in the compositions of agents delaying absorption, for example, aluminium monostearate and gelatine.

Sterile injectable solutions may be prepared by incorporating the active compounds in the required amount in an appropriate solvent with various of the other ingredients enumerated above, as required, followed by filtered sterilisation. Generally, dispersions are prepared by incorporating the compound into a sterile vehicle that contains the basic dispersion medium and the other ingredients. In the case of sterile powders for the preparation of sterile injectable solutions, the preferred methods of preparation are vacuum drying and freeze-drying techniques that yield a powder of the compound plus any additional desired ingredient from previously sterile-filtered solution thereof.

Thus, the present invention also provides an injectable, stable, sterile composition comprising a compound of Formula A, or a salt thereof, in a unit dosage form in a sealed container. The compound or salt may be provided in lyophilised form capable of being reconstituted with a suitable pharmaceutically acceptable carrier to form a liquid composition suitable for injection thereof into a subject. The unit dosage form typically comprises from about 10 mg to about 10 grams of the compound or salt thereof. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

(d) Aerosols

Pharmaceutical compositions are also provided which are suitable for administration as an aerosol, by inhalation. These compositions comprise a solution or suspension of the desired compound or a salt thereof or a plurality of solid particles of the compound or salt. The desired composition may be placed in a small chamber and nebulized. Nebulization may be accomplished by compressed air, or by ultrasonic energy to form a plurality of liquid droplets or solid particles comprising the compounds or salts.

The solid particles can be obtained by processing solid compound or a salt thereof, in any appropriate manner known in the art, such as by micronization. Commercial nebulizers are also available to provide liquid droplets of any desired size.

The liquid droplets or solid particles should have a particle size in the range of about 0.5 to about 5 microns, preferably from about 1 to about 2 microns. Most preferably, the size of the solid particles or droplets will be from about 1 to about 2 microns. Such particles or droplets may be dispensed by commercially available nebulisers or by other means known to the skilled person.

When the pharmaceutical composition suitable for administration as an aerosol is in the form of a liquid, the composition will comprise a water-soluble form of the compound or a salt thereof, in a carrier that comprises water. A surfactant may be present which lowers the surface tension of the composition sufficiently to result in the formation of droplets within the desired size range when subjected to nebulization.

In addition, the pharmaceutical composition may also include other agents. For example, preservatives, co-solvents, surfactants, oils, humectants, emollients, chelating agents, dyestuffs, stabilizers or antioxidants may be employed. Water soluble preservatives that may be employed include, but are not limited to, benzalkonium chloride, chlorobutanol, thimerosal, sodium bisulfate, phenylmercuric acetate, phenylmercuric nitrate, ethyl alcohol, methylparaben, polyvinyl alcohol, benzyl alcohol and phenylethyl alcohol. A surfactant may be Tween 80. Other suitable additives include lubricants and slip agents, such as, for example, magnesium stearate, stearic acid, talc and bentonites, substances which promote disintegration, such as starch or crosslinked polyvinylpyrrolidone, binders, such as, for example, starch, gelatin or linear polyvinylpyrrolidone, and dry binders, such as microcrystalline cellulose.

Other vehicles that may be used include, but are not limited to, polyvinyl alcohol, povidone, hydroxypropyl methyl cellulose, poloxamers, carboxymethyl cellulose, hydroxyethyl cellulose, purified, water, etc. Tonicity adjustors may be included, for example, sodium chloride, potassium chloride, mannitol, glycerin, etc. Antioxidants include, but are not limited to, sodium metabisulfite, sodium thiosulfate, acetylcysteine, butylated hydroxyanisole, butylated hydroxytoluene, etc. The indications, effective doses, compositions, contraindications, vendors etc, of the compounds in the compositions are available or are known to one skilled in the art. These agents may be present in individual amounts of from about 0.001% to about 5% by weight and preferably about 0.01% to about 2%.

Electrolytes such as, but not limited to, sodium chloride and potassium chloride may also be included in the composition.

Further, the compositions may contain microbial preservatives. Useful microbial preservatives include methylparaben, propylparaben, and benzyl alcohol. The microbial preservative is typically employed when the composition is placed in a vial designed for multidose use.

Excipients which may be used are all the physiologically acceptable solid inert substances, either inorganic or organic in mature. Inorganic substances are, for example, sodium chloride, carbonates, such as calcium carbonate, bicarbonates, aluminium oxides, silicic acids, aluminas, precipitated or colloidal silicon dioxide and phosphates. Organic substances are, for example, sugars, cellulose, foodstuffs and feedstuffs, such as milk powder, animal flours, cereal flours and shredded cereals and starches.

Finally, it will be appreciated that the compositions of the present invention may comprise a plurality of compounds as described herein.

Compounds

In one form, the invention provides a compound of Formula B:

(Formula B)

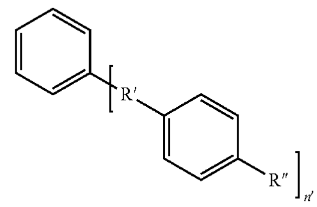

Where:

N'=2, 3 or 4

R' comprises any one of $C_2$-alkyl, $C_2$-alkene or $C_2$-alkyne; and

R" is independently selected from $NH_2$, $CH_3$, OH, $—COCH_3$, $—OC(CH_3)_3$, $OCH_3$, $OCH_2CH_3$, $OCH(CH_3)_2$, $—CONH_2$, COOH, $COOCH_3$, or $COOCH_2CH_3$.

In a preferred form, the invention provides a compound of Formula B:

(Formula B)

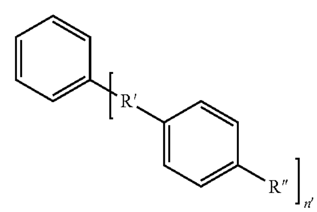

wherein

R' comprises any one of $C_2$-alkyl, $C_2$-alkene; and

R" is independently selected from COOH, $COOCH_3$, or $COOCH_2CH_3$.

Preferably, where n'=2, R'—$C_6H_4$—R", is substituted at positions 1 and 3.

Preferably, where n'=3, R'—$C_6H_4$—R", is substituted at positions 1, 3 and 5; or 1, 2 and 4.

Preferably, where n'=3, R'—$C_6H_4$—R", is substituted at positions 1, 2, 4 and 5.

In accordance with a further aspect of the present invention, there is provided a compound of Formula C:

(Formula C)

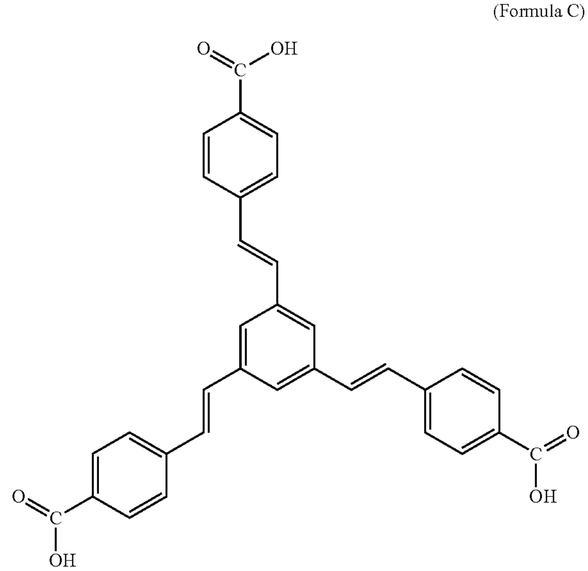 [SMILES: O=C(O)c1ccc(/C=C/c2cc(/C=C/c3ccc(C(=O)O)cc3)cc(/C=C/c3ccc(C(=O)O)cc3)c2)cc1]

The compounds of the present invention may be provided in the form of a pharmaceutically acceptable salt.

Pharmaceutically acceptable salts for the purposes of the present invention include non-toxic cation and anion salts. Examples include, but are not limited to sodium, potassium, aluminium, calcium, lithium, magnesium, zinc and from bases such as ammonium, ethylenediamine, N-methyl-glutamine, lysine, arginine, ornithine, choline, N, N'-dibenzylethlenediamine, diethylamine, piperazine, tris(hydroxymethyl)aminomethane, tetramethylammonium, acetate, lactobionate, benzenesulfonate, laurate, benzoate, malate, bicarbonate, maleate, bisulfate, mandelate, bitratrate, meyate, borate, methylbromide, bromide, methylnitrate, calcium edetate, methylsulfate, camsylate, mucate, carbonate, napsylate, chloride, nitrate, clavulanate, N-methylglucamine, citrate, hydrochloride, oleate, edetate, oxalate, edisylate, pamoate (embonate), estolate, palmitate, esylate, pantothenate, fumarate, phosphate, diphosphate, glucepate, plygalacturonate, gluconate, salicylate, glutamate, stearate, glycollylarsanilate, sulfate, hexylresorcinate, subacetate, hydrabamine, succinate, hydrobromide, tannate, tartrate, hydroxynapthoate, teoclate, iodide, tosylate, isothionate, triethiodide, lactate, panoate and valerate.

In an alternative aspect, the compound provided by the present invention is preferably selected from the following list of analogues of compound C: TSB049, TSB063, TSB037, TSB041, TSB019, TSB023, TSB025, TSB065, TCT003, TSB001, TSB009, TSB053, TAB001, TCB001, TCB003 (see FIGS. 8 to 12 for structure information). More preferably, the compound is TSB065 or TCB001.

EXAMPLES

The present invention is not to be limited in scope by the specific embodiments described herein, which are intended for the purpose of exemplification only. Functionally equivalent products, compositions and methods are clearly within the scope of the invention as described herein.

Example 1

Synthesis of Compounds

The compounds of the present invention are synthesised using the Heck Cross Coupling method.

Figure 1:
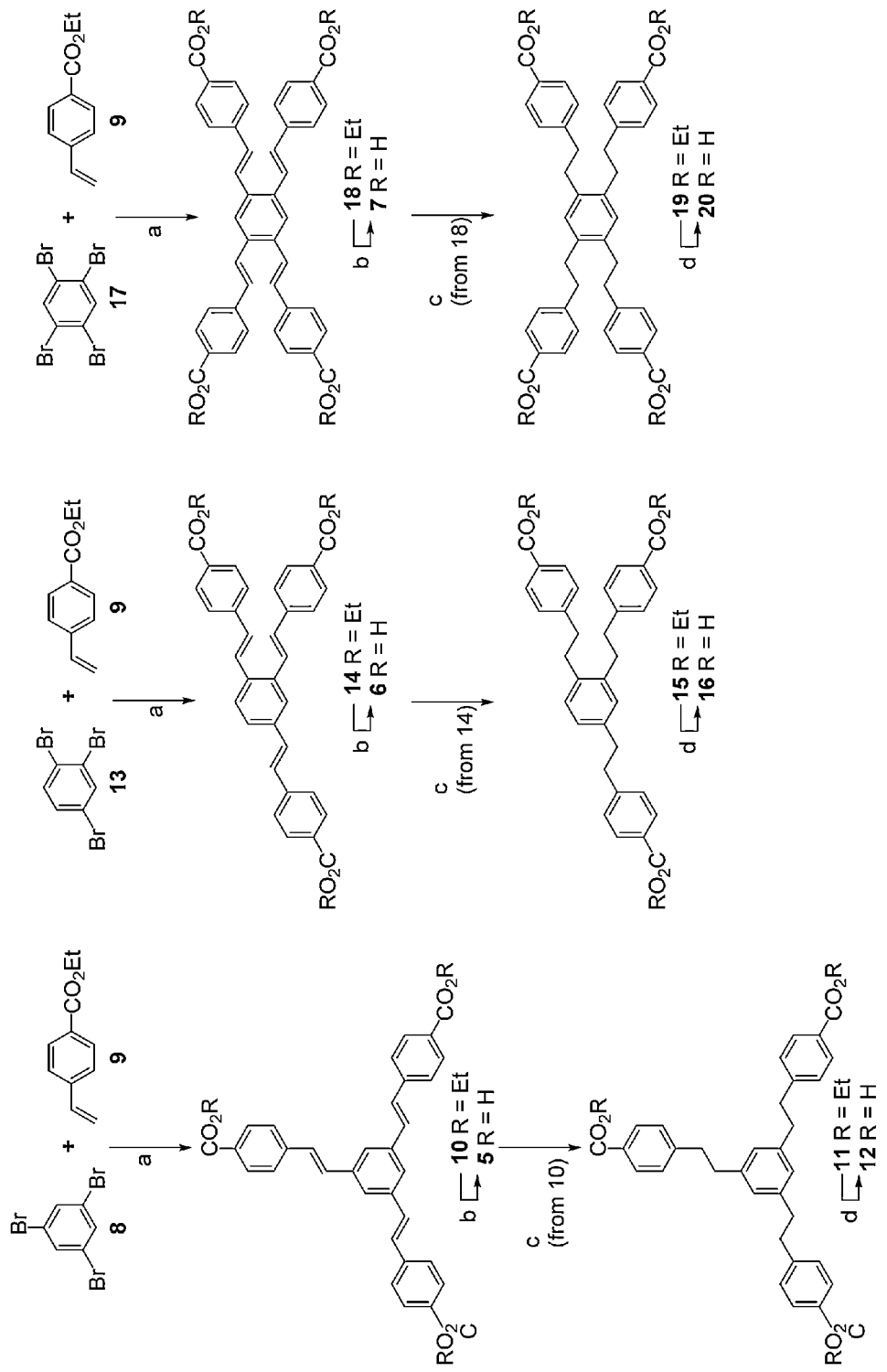
FIGS. 1 and 2 provide general pathways for synthesis of the target compounds through the Heck Cross coupling approach.
Figure 2:
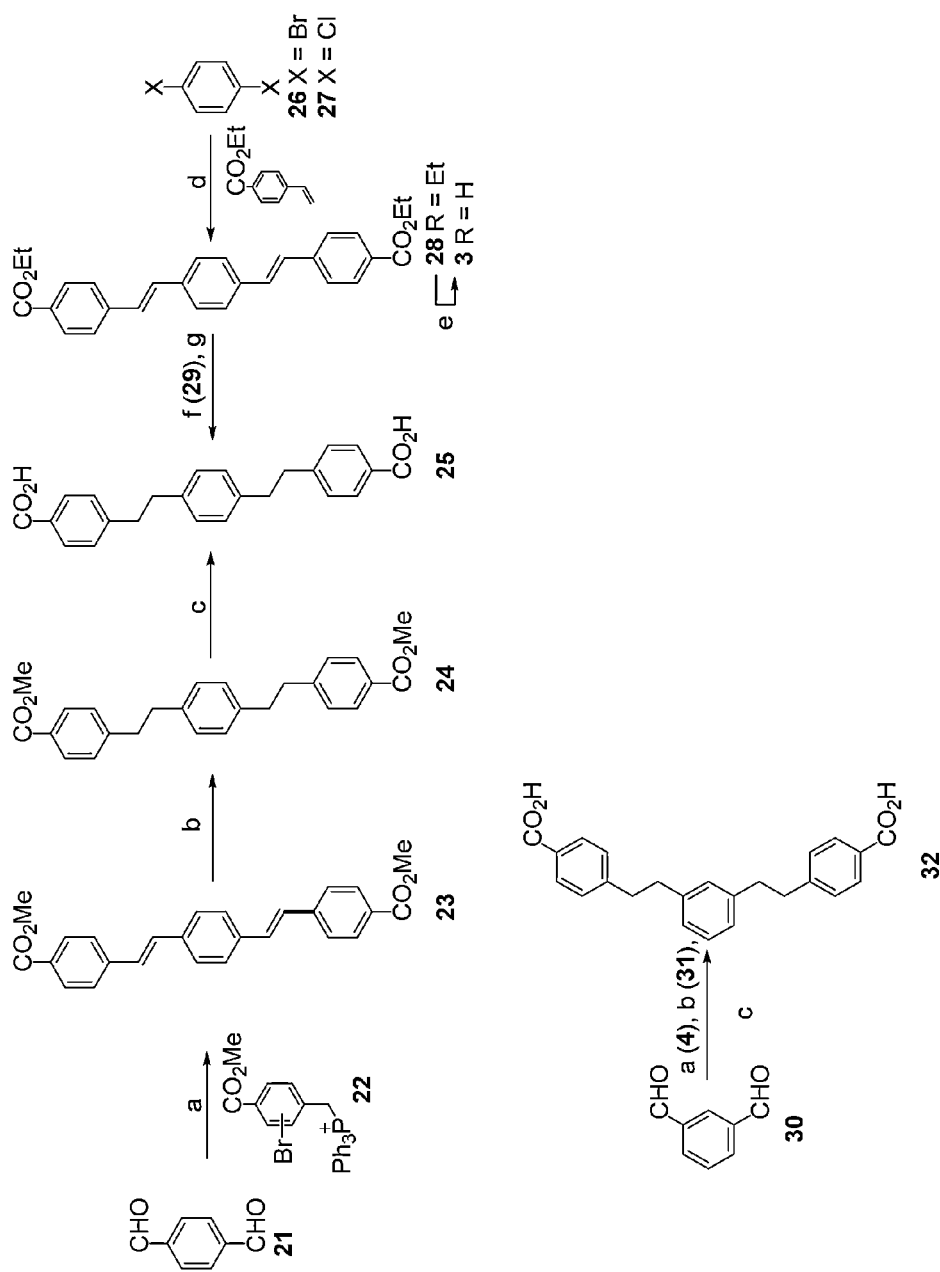

Generally, the pathways for synthesis are as shown in FIGS. 1 and 2—the synthesis of the target compounds through the Heck Cross coupling approach. The reagents and reaction conditions for the chemical transformations shown in these figures are denoted by a letter for each reaction. The key for this labelling is:

For FIG. 1: (a). $Pd_2(dba)_3/[(t-Bu)_3PH]BF_4$, Tetrahydrofuran ("THF"), reflux, 17 h (82-97%) (b) LiOH, $H_2O$/EtOH, reflux, 3 hrs (c) Pd/C—$H_2$, $CH_2Cl_2$/EtOH, 17 h (d) LiOH, $H_2O$/EtOH, reflux, 3 hrs For FIG. 2: (a) NaOMe, MeOH, 22, rt. 17 h, 84% (b) Pd/C (10% w/w), $H_2$, 1:1 $CH_2Cl_2$/MeOH, 17 h, rt, 93% (c) LiOH, MeOH/$H_2O$, reflux, 97% (d) $Pd_2(dba)_3$·$CHCl_3$, $[(t-Bu)_3PH]BF_4$, $Cy_2NMe$, THF, reflux, 17 h, 84% from 26, 72 h, 29% from 27 (e) LiOH, 9:1 EtOH/$H_2O$, reflux, 17 h, 66% (f) Pd/C, $H_2$, 1:1 $CH_2Cl_2$/EtOH, 17 h, 96% (g) LiOH, EtOH/$H_2O$, reflux, 17 h, 82%.

General Conditions

Terephthaldehyde, tributylphosphonium tetrafluoroborate, 1,3,5-tribromobenzene and 1,2,4-tribromobenzene were purchased from the Sigma-Aldrich Chemical Company. Dry THF was distilled from sodium benzophenone ketyl radical and stored over a sodium mirror. N-Methyldicyclohexylamine was distilled under reduced pressure and stored under argon. Dess-Martin Periodinane, Herrmann-Beller paladacycle [Herrmann et al. Chem. Int. Ed. Engl. 1995, 34, 1844-1849] (methyl 4-carboxybenzyl)triphenylphosphonium bromide, $Pd_2(dba)_3$·$CHCl_3$, and $Pd(PPh3)_4$ were prepared as described previously [Ukai et al. Organomet. Chem. 1974, 65, 253-266; Coulson, D. R. Inorg. Synth. 1972, 13, 121-123]. 1,3-di(hydroxymethyl)benzene was prepared by the $LiAlH_4$ reduction of dimethyl 1,3-benzenedicarboxylate in a similar procedure to the 1,2-isomer [Sharpless, K. B.; Oi, R. Org. Synth. 1996, 73, 1-13] Ethyl 4-vinylbenzoate was prepared by the Fischer esterification of 4-vinyl benzoic acid [Broos et al. J. Chem. Ed. 1978, 55, (12), 813. 33; Tullen et al. J. Chem. Ed. 1971, 48, (7)].

NMR spectra were acquired on either a Bruker AV500 ($^1H$ at 500.13 MHz, $^{13}C$ at 125.8 MHz) or a Bruker AV600 ($^1H$ at 600.13 MHz, $^{13}C$ at 150.9 MHz) and all signals δ are reported in parts per million (ppm). $^1H$ and $^{13}C$ assignments were made with the aid of DEPT, COSY, HSQC and HMBC sequences where appropriate. $^1H$ spectra were referenced to residual (partially) undeuterated solvents, $CDCl_3$ ($CHCl_3$ at 7.26 ppm) and $d_6$-DMSO ($d_5$-DMSO at 2.50 ppm (pentet)). $^{13}C$ spectra were referenced to the deuterated solvents, $CDCl_3$ at 77.16 ppm and $d_6$-DMSO at 39.52 ppm.

Infrared spectra samples were prepare using the KBr disc method and samples acquired on a Perkin Elmer. Spectrum One spectrometer at 2 $cm^{-1}$ resolution. Electronic spectra were collected using a HP8452 spectrophotometer in 1 cm quartz cells at ~1×10$^{-5}$ or ~1×10$^{-6}$ MolL$^{-1}$ in the solvents indicated: Fluorescence spectra were recorded at 1×10$^{-7}$ MolL$^{-1}$.

Mass spectra were acquired on a VG Autospec employing the electron impact (EI) ionization mode.

Standard Conditions for Heck Cross-Coupling Procedure

To a flame-dried schlenk flask was added the halobenzene (1 equiv), Pd$_2$(dba)$_3$.CHCl$_3$ (2-15 mol %) and [(t-Bu)$_3$PH]BF$_4$ (10-60 mol %) which were subsequently dried under vacuum for 15 minutes before being dissolved in dry THF. N-Methyldicyclohexylamine (4 equiv) and ethyl 4-vinylbenzoate 7 (3.3 equiv) were added via syringe and the reaction monitored by TLC (neat CH$_2$Cl$_2$). Upon completion of the reaction the residual THF was removed in vacuo, the crude material redissolved in CH$_2$Cl$_2$ and filtered to remove any insoluble material before being absorbed onto fine silica and eluting with 0:100 to 2:98 MeOH/CH$_2$Cl$_2$.

Standard Method for Reduction of Alkenes

The alkene was loaded into a glass autoclave tube and dissolved/suspended in 1:1 CH$_2$Cl$_2$/MeOH or 1:1 CH$_2$Cl$_2$/EtOH depending upon the ester present. Argon was bubbled through the mixture for 10 minutes before 10% Pd/C (~10 wt % of alkene) was added, and the flask pressurized with H$_2$ (50 atm). The reaction was allowed to proceed for 17 h before being depressurized, purged with argon, filtered through a pad of celite and concentrated under reduced pressure. Further purification is described for each compound when necessary.

Standard Method for Saponification Reactions

The ester (1 equiv) and LiOH (2 equiv per ester) were dissolved in 9:1 H$_2$O/MeOH or H$_2$O/EtOH depending upon the ester and refluxed overnight. After cooling to room temperature the solvent was removed under reduced pressure, the remaining solution diluted with H$_2$O, cooled in an ice-bath and the pH adjusted to 3 by the addition of HCl (1M). The precipitate was collected filtered and product dried under vacuum.

1,3,5-Tris[(1E)-2'-(ethyl 4"-benzoate)vinyl]benzene (10)

Prepared as per, the standard procedure using 1,3,5-tribromobenzene 8 (1010 mg, 3.21 mmol), Pd$_2$(dba)$_3$.CHCl$_3$ (882 mg, 0.85 mmol), t-Bu$_3$PHBF$_4$ (560 mg, 1.93 mmol), Cy$_2$NMe (3.0 mL), ethyl 4-vinylbenzoate 7 (1870 mg, 10.61 mmol) and THF (40 mL). The product was eluted with 2:98 MeOH/CH$_2$Cl$_2$ and recrystallized from CH$_2$Cl$_2$/EtOH to give 10 as an off white powder, 1.86 g (97%).

$^1$H NMR (600 MHz, CDCl$_3$): δ 1.42 (t, J=7.1 Hz, 9H, CH$_3$), 4.40 (q, J=7.1 Hz, 6H, CH$_2$), 7.24 (AB quartet, 6H, vinyl), 7.60 (d, J=8.3 Hz, 6H, ArH), 7.61 (s, 3H, ArH), 8.06 (d, J=8.3 Hz, 6H, ArH).

$^{13}$C NMR (150 MHz, CDCl$_3$): δ 14.51 (CH$_3$), 61.13 (CH$_2$), 125.0 (CH), 126.5 (CH), 128.7 (CH), 129.7 (C), 130.2 (CH), 130.5 (CH), 137.9 (C), 141.5 (C), 166.5 (C=O).

IR (KBr): ν (cm$^{-1}$) 2979, 2929, 1713, 1604, 1279, 1178, 1105, 762, 698

HR-EI$^+$-MS: C$_{39}$H$_{36}$O$_6$ requires 600.2512 amu, found 600.2513.

EI$^+$-MS: MI$^+$=C$_{39}$H$_{36}$O$_6$; m/z: 600.3 (100%)=MI$^+$, 555.2 (7%)=[MI-EtO]$^+$.

UV-Vis (CH$_2$Cl$_2$): λ (nm) [log ε(M$^{-1}$cm$^{-1}$)] 258 [4.49], 330 [4.28]

Fluorescence (CH$_2$Cl$_2$): excitation (nm) [emission (nm)] 258 [397, 418, 518], 330 [397, 418]; (cyclohexane) 328 [393, 413]

1,3,5-Tris[(1E)-2'-(4"-benzoic acid)vinyl]benzene (5)

Using the standard saponification procedure, 10 (252.1 mg, 0.42 mmol), LiOH.H$_2$O (112.0 mg, 2.7 mmol) and 1:9 H$_2$O/EtOH (20 mL) gave an gelatinous precipitate that was collected and recrystallised from THF/H$_2$O and dried to give the triacid 5 as a pale brown powder, 209 mg (95%).

$^1$H, NMR (500.1 MHz, d$_6$-DMSO): δ 7.49 (m, 6H, vinyl CH), 7.76 (d, J=8.5 Hz, 6H, ArH), 7.88 (s, 3H, core ArH), 7.98 (d, J=8.5 Hz, 6H, ArH).

$^{13}$C NMR (125.8 MHz, d$_6$-DMSO): δ (ppm) 125.0, 126.5, 128.4, 129.7, 129.9, 130.50, 137.6, 141.3, 167.1.

IR (KBr): ν (cm$^{-1}$) 3067, 3026, 1684 (ν$_{C=O}$), 1604, 1566, 1420, 1384, 1312, 1286, 1179.

HR-EI$^+$-MS: C$_{33}$H$_{24}$O$_6$ requires 516.1573 amu. found 516.1564.

EI$^+$-MS: MI=C$_{33}$H$_{24}$O$_6$; m/z: 516.1 (100%)=MI$^+$, 472.1 (11.3%)=[MI-CO$_2$]$^+$ 1,3,5-Tris[(1E)-2'-(ethyl 4"-benzoate)ethyl]benzene (11)

Conducted as per the standard reduction procedure with trimester 10 (251 mg, 0.42), Pd/C (20 mg) and 1:1 CH$_2$Cl$_2$/EtOH (15 mL). The crude product was recrystallized from CH$_2$Cl$_2$/EtOH to give the triester 11 237 mg (93%) of a white solid.

$^1$H-NMR (600 MHz, CDCl$_3$): δ 1.38 (t, J=7.1 Hz, 9H, CH$_3$), 2.87 (m, 12H, bridge CH$_2$), 4.36 (q, J=7.1 Hz, 6H, CH$_2$), 6.76 (s, 3H), 7.20 (d, J=8.1 Hz, 6H, ArH), 7.97 (d, J=8.1 Hz, 6H, ArH).

$^{13}$C NMR (150 MHz, CDCl$_3$): δ 14.4, 37.5, 38.0, 60.8, 126.5, 128.3, 128.6, 129.7, 141.4, 147.2, 166.7.

HR-EI-MS: C$_{39}$H$_{42}$O$_6$ requires 606.2981 amu. found 606.2994.

1,3,5-Tris[2'-(4"-benzoic acid)ethyl]benzene (12)

Using the standard procedure triester 11 (252.0 mg, 0.42 mmol), LiOH.H$_2$O (107.2 mg, 2.6 mmol) and 1:9 H$_2$O/EtOH (20 mL) gave triacid 3 202 mg (93%) as a white powder.

$^1$H-NMR (500 MHz, d$_6$-DMSO): δ 2.82 (cm, 12H, CH$_2$), 6.83 (s, 3H, ArH), 7.28 (d, J=8.2 Hz, 6H, ArH), 7.85 (d, J=8.2 Hz, 6H, ArH).

$^{13}$C NMR (125 MHz, CDCl$_3$): δ 36.7, 37.1, 126.2, 128.4, 126.2, 129.3, 140.9, 146.9, 167.3.

IR (KBr): ν (cm$^1$) 3067, 2929, 1686, 1610, 1422, 1315, 1288, 1179.

HR-EI$^+$-MS: C$_{33}$H$_{30}$O$_6$ requires 522.2042 amu. found 522.5897.

EI$^+$-MS: MI$^+$=C$_{33}$H$_{30}$O$_6$; m/z: 504.2 (90%)=[MI-H$_2$O]$^+$, 387.1 (100%)=[MI-CH$_2$(C$_6$H$_4$CO$_2$H)]$^+$.

1,2,4-Tris[(1E)-2'-(ethyl 4"-benzoate)vinyl]benzene (14)

Using the standard Heck cross-coupling procedure, 1,2,4-tribromobenzene 13 (1.018 g, 3.2 mmol), ethyl 4-vinyl-benzoate 9 (1.843 g, 10.5 mmol), Pd$_2$(dba)$_3$.CHCl$_3$ (87.6 mg, 0.08 mmol), [(t-Bu)$_3$PH]BF$_4$ (122.6 mg, 0.42 mmol), Cy$_2$NMe (3 mL) in THF (40 mL) were heated for 17 h. The crude mixture was subjected to flash chromatography eluting with neat CH$_2$Cl$_2$. The crude product was recrystallised from CH$_2$Cl$_2$/EtOH to give 1.681 g (88%) of a pale yellow solid.

$^1$H NMR (600 MHz, CDCl$_3$): δ 1.409, 1.413, 1.416 (3×t, J=7.1 Hz, 9H, CH$_3$), 4.392, 4.394, 4.400 (3×q, J=7.1 Hz, 6H, CH$_2$) 7.06-7.11 (m, 2H, vinyl CH), 7.17-7.28 (m, 2H, vinyl CH), 7.51-7.67 (cm, 9H), 7.73 (m, 1H, core ArH), 8.04-8.09 (cm, 6H, ArH).

$^{13}$C NMR (150 MHz, CDCl$_3$): δ 14.5 (CH$_3$), 61.1, 61.13, 61.1 (CH$_2$), 125.8 (CH), 126.5 (CH), 126.5 (CH), 126.6 (CH), 126.4 (CH), 127.3 (CH), 128.3 (CH), 128.4 (CH), 128.7 (CH), 129.6 (C), 129.8 (C), 129.8 (C), 130.2 (CH), 130.2 (CH), 130.3 (CH), 130.5 (C), 130.7 (C), 131.3 (C), 135.6 (C), 136.4 (C), 136.9 (C), 141.62 (C=O), 141.66 (C=O), 141.7 (C=O).

IR (KBr): ν (cm$^{-1}$) 2981, 1713 (ν$_{C=O}$), 1604, 1278, 1178, 1107

HR-EI$^+$-MS: C$_{39}$H$_{36}$O$_6$ requires 600.2512 amu. found 600.2504.

EI$^+$-MS: MI=C$_{39}$H$_{36}$O$_6$; Mk: 600.2 (100%)=MI$^+$, 555.2 (13.3%)=[MI-EtO]$^+$, 437.1 (70.1%)=[MI-2×OEt-EtO$_2$CH]$^+$

UV-Vis (Solv): λ (nm) [ε, (M$^{-1}$cm$^{-1}$)] 258 [4.53], 338 [4.83], 362 [4.76, shoulder].

Fluorescence (CH$_2$Cl$_2$): excitation (nm) [emission (nm)] 258 [436 (shoulder), 450], 338 [436 (shoulder), 450]; (cyclohexane) 334 [416, 440]

1,2,4-Tris[(1E)-2'-(4"-benzoic acid)vinyl]benzene (6)

Triester 14 (250 mg, 0.42 mmol) and LiOH.H$_2$O (70.2 mg, 1.67 mmol) in 9:1 EtOH/H$_2$O were treated as described in the general saponifiaction procedure giving the triacid 6 186.6 mg (86%) as a, yellow/brown solid.

IR (KBr): ν (cm$^{-1}$) 2929, 1684 (ν$_{C=O}$), 1603, 1419, 1315, 1287, 1178, 1125, 763.

1,2,4-Tris[2'-(ethyl 4"-benzoate)ethyl]benzene (15)

Triester 14 (306 mg, 0.51 mmol) and Pd/C (10% w/w, ca 40 mg) in 1:1 EtOH/CH$_2$Cl$_2$ (20 mL) was treated as described. The crude product was recrystallised from THF and hexane to give ester 15 305 mg (98%).

$^1$H-NMR (600 MHz, CDCl$_3$): δ 1.376, 1.381, 1.393 (3×t, 3×CH$_3$, 9H) 2.79-2.95 (m, 12H), 4.33-4.40 (m, 6H), 6.86 (s, 1H), 6.95 (d, J=7.8 Hz, 1H), 7.04 (d, J 7.8 Hz, 1H), 7.17 (AB d, J=8.0 Hz, 2H), 7.19 (AB d, J=8.0 Hz, 2H) 7.21 (AB d, J=8.1 Hz, 2H), 7.95 (cm, J=7.7 Hz, 6H)

$^{13}$C NMR (150 MHz, CDCl$_3$): δ 14.48, 14.50, 34.0, 34.4, 37.2, 37.7, 38.1, 61.0, 61.0, 126.6, 128.43, 128.54, 128.56, 128.7, 129.5, 129.7, 129.8, 129.9, 136.7, 139.0, 139.3, 147.2, 147.2, 147.3, 166.7, 166.8, 166.8.

IR (KBr): ν (cm$^{-1}$) 2981, 2942, 1713, 1610, 1283, 1177, 1123, 1108.

HR-EI$^+$-MS: C$_{39}$H$_{42}$O$_6$ requires 606.2981 amu. found EI$^+$-MS: MI=C$_{39}$H$_{42}$O$_6$; m/z: (%)=(%)=[MI-]$^+$

1,2,4-Tris[2'-(4"-benzoic acid)ethyl]benzene (16)

Triester 15 (200 mg, 0.33 mmol) and LiOH.H$_2$O (92.2 mg, 2.15 mmol) in 9:1 EtOH/H$_2$O (25 mL) was treated as described in the general saponification procedure, giving triacid 16 161 mg (94%).

$^1$H NMR (500.1 MHz, d$_6$-DMSO): δ 2.77-2.91 (m, 12H, methylene), 6.960 (AB, J=8.5 Hz, 1H), 6.967 (s, 1H), 7.07 (AB, J=8.5 Hz, 1H), 7.271 (AB, J=8.4 Hz, 2H), 7.296 (AB, J=8.4 Hz, 2H), 7.299 (AB, J=8.4 Hz, 2H), 7.82-7.87 (m, 6H), 12.83 (br s, CO$_2$H).

$^{13}$C NMR (125.8 MHz, d$_6$-DMSO): δ 33.1, 33.5, 36.3, 36.7, 37.0, 126.2, 128.5, 128.6, 128.6, 128.6, 129.0, 129.3, 129.4, 136.4, 138.6, 138.7, 146.9, 146.9, 167.3, 167.3.

IR (KBr): ν (cm$^{-1}$), 1688, 1610, 1422, 1315, 1289, 1178.

HR-EI$^+$-MS: C$_{33}$H$_{30}$O$_6$ requires 522.2042 amu. found 522.2045.

EI$^+$-MS: MI=C$_{33}$H$_{30}$O$_6$; m/z: 522.2 (9%)=MI$^+$, 504.2 (86%)=[MI-H$_2$O]$^+$, 387.1 (100%)=[MI-CH$_2$(C$_6$H$_4$CO$_2$H)]$^+$.

1,2,4,5-Tetrakis[(1E)-2'-(ethyl 4"-benzoate)vinyl]benzene (18)

1,2,4,5-tetrabromobenzene 17 (255.8 mg, 0.66 mmol), ethyl-4-vinylbenzoate 9 (498.6 mg, 2.83 mmol), Pd$_2$(dba)$_3$.CHCl$_3$ (69.2 mg, 0.07 mmol), [(t-Bu)$_3$PH]BF$_4$ (75.4 mg, 0.26 mmol), Cy$_2$NMe (0.8 mL) in THF (8 mL) were treated under the aforementioned cross-coupling procedure. The product was purified by flash chromatography with CH$_2$Cl$_2$/MeOH (100:0-99:1) an the eluent. The crude material was recrystallized from CH$_2$Cl$_2$/EtOH to give triester 18 541.2 mg (82%) as a bright yellow solid.

$^1$H NMR (600 MHz, CDCl$_3$): δ 1.41 (t, J=7.1 Hz, 12H, CH$_3$), 4.40 (q, J=7.1 Hz, 8H, CH$_2$), 7.13 (d, J=16 Hz, 4H, vinyl CH), 7.56 (d, J=16.1 Hz, 4H, vinyl CH), 7.60 (d, J=8.3 Hz, 8H, ArH), 7.83 (s, 2H, core ArH), 8.06 (d, J=8.3 Hz, 4H, ArH).

$^{13}$C NMR (150 MHz, CDCl$_3$): δ 14.3 (CH$_3$), 61.0 (CH$_2$), 125.2 (ArCH, core), 126.5 (ArCH), 128.1 (CH, vinyl), 129.7 (C$_q$), 130.1 (ArCH), 131.0 (CH, vinyl), 135.5 (C), 141.4 (C), 166.3 (C=O).

IR (KBr): ν (cm$^{-1}$) 2981, 1710, 1637, 1617, 1604, 1282, 1180, 1107.

HR-EI$^+$-MS: C$_{50}$H$_{46}$O$_8$ required 774.3193 amu. found 774.3506 amu.

EI$^+$-MS: MI=C$_{50}$H$_{46}$O$_8$; m/z: 774.4 (100%)=MI$^+$, 729.1 (16%)=[MI-OEt]$^+$, 611.1 (45%)=[MI-CH$_2$(C$_6$H$_4$CO$_2$Et)]$^+$.

UV-Vis (Solv): λ (nm) [log ε(M$^{-1}$ cm$^{-1}$)] 258 [4.62], 312 [4.73], 346 [4.82].

Fluorescence (CH$_2$Cl$_2$): excitation (nm) [emission (nm)] 258 [455, 518], 312 [362, 381, 452], 346 [381, 454]; (cyclohexane) 336 [442].

1,2,4,5-Tetrakis[(1E)-2'-(4"-benzoic acid)vinyl)]benzene (7)

Triester 18 (151.7 mg, 0.20 mmol), LiOH.H$_2$O (86.6 mg, 2.06 mmol) in 9:1 EtOH/H$_2$O (30 mL) were treated as described in the general saponification procedure. The crude product was recrystallized from THF and MeOH to give triacid 7 111.3 mg (85%) as a tan powder.

$^1$H NMR (500 MHz, CDCl$_3$): δ (d, J=Hz, 6H, ArH), (s, 3H, ArH), (d, J=Hz, 6H, Ark $^{13}$C NMR (125.8 MHz, CDCl$_3$): δ (ppm), 124.2, 127.1, 127.6 (CH), 129.5, 129.9, 130.7, 135.3, 141.5, 167.2.

IR (KBr): ν (cm$^{-1}$)

HR-EI$^+$-MS: C$_{42}$H$_{30}$O$_8$ requires 662.1941 amu,

1,2,4,5-Tetrakis[(2'-(ethyl 4"-benzoate)ethyl)benzene (19)

Triester 18 (200.4 mg, 0.24 mmol) and Pd/C (10% w/w, c.a. 30 mg) in 1:1 EtOH/CH$_2$Cl$_2$ (40 mL) was treated as described. The crude product was recrystallized from $CH_2Cl_2$ and EtOH to give compound 19 147.1 mg (79%) as a white solid.

$^1$H NMR (600 MHz, $CDCl_3$): δ 1.38 (t, J=7.2 Hz, 12H), 2.82 (m, 16H), 4.36 (q, J=7.2 Hz, 8H), 6.81 (s, 2H), 7.18 (d, J=8.0 Hz, 8H, ArH), (s, 3H, ArH), (d, J=Hz, 6H, ArH).

$^{13}$C NMR (150 MHz, $CDCl_3$): δ 14.8, 34.0, 37.8, 61.0, 128.5, 128.6, 129.8, 130.6, 136.9, 147.2, 166.7.

IR (KBr): ν ($cm^{-1}$) 2980, 2935, 1716, 1611, 1285, 1176, 1107, 1022

HR-EI$^+$-MS: $C_{50}H_{54}O_8$ requires 782.3819 amu,

1,2,4,5-Tetrakis[2'-(4"-benzoic acid)ethyl]benzene (20)

Triester 19 (101.4 mg, 0.13 mmol), LiOH.$H_2O$ (51 mg, 1.22 mmol) in 9:1 EtOH/$H_2O$ (25 mL) were treated as described in the general saponification procedure, to give tetraacid 20 87.3 mg (97%) as a white solid.

$^1$H NMR (500.1 MHz, $d_6$-DMSO): δ 2.77 (s, 16H, $CH_2CH_2$), 6.86 (s, 2H, H2), 7.26 (AB, J=8.3 Hz, 8H, H2') 7.84 (AB, J=8.3 Hz, 8H, H3').

$^{13}$C NMR (125.8 MHz, $d_6$-DMSO): δ 33.1, 36.8, 128.5, 128.6, 129.4, 136.3, 147.0, 167.3.

IR (KBr): ν ($cm^{-1}$) 2945, 2863, 1688, 1610, 1422, 1315, 1288, 1178.

HR-EI$^+$-MS: $C_{42}H_{38}O_8$ requires 670.2567 amu. found 670.2562.

EI$^+$-MS: MI=$C_{42}H_{38}O_8$; m/z: 517.0 (100%)=[MI-$H_2O$—($CH_2(C_6H_4CO_2H)$)]$^+$, 499.0 (12%)=[MI-2($H_2O$)—($CH_2(C_6H_4CO_2H)$)]$^+$, 381.0 (19.5%)=[MI-$H_2O$-2($CH_2(C_6H_4CO_2H)$)]$^+$, 135.0=[($CH_2(C_6H_4CO_2H)$)]$^+$.

1,4-Bis[(1E)-2'-(ethyl 4"-benzoate)vinyl]benzene (28)

Method A: 1,4-Dibromobenzene 26 (101.5 mg, 0.43 mmol), ethyl 4-vinyl benzoate 7 (166 mg, 0.94 mmol), $Pd_2(dba)_3$.$CHCl_3$ (45.1 mg, 0.04 mmol), [(t-Bu)$_3$PH]$BF_4$ (52.2 mg, 0.18 mmol), $Cy_2NMe$ (300 □l) in THF (5 mL) were heated at reflux overnight. The THF was removed under reduced pressure, the crude product purified using flash chromatography with $CH_2Cl_2$ as the eluent. Additional recrystallisation from $CH_2Cl_2$ and EtOH, gave 28 152.2 mg (84%).

Method B: 1,4-dichlorobenzene 27 (59.9 mg, 0.41 mmol), ethyl 4-vinyl benzoate 7 (160 mg, 0.91 mmol), $Pd_2(dba)_3$.$CHCl_3$ (42.1 mg, 0.04 mmol), [(t-Bu)$_3$PH]$BF_4$ (47.7 mg, 0.16 mmol), $Cy_2NMe$ (300 □l) in THF (5 mL) were heated at reflux for 3 days. The reaction mixture was concentrated under reduced pressure, the crude product was purified by chromatography with $CH_2Cl_2$ as the eluent. Additional recrystallisation from $CH_2Cl_2$ and EtOH, gave 28 49.8 mg (29%).

$^1$H NMR (600 MHz, $CDCl_3$): δ 1.41 (t, J=7.1 Hz, 6H), 4.39 (q, J=7.1 Hz, 4H), 7.14 (AB, J=16.3 Hz, 2H, vinyl CH), 7.24 (AB, J=16.3 Hz, 2H, vinyl CH), 7.55 (s, 4H), 7.57 (d, J=8.1 Hz, 4H), 8.04 (d, J=8.1 Hz, 4H).

$^{13}$C NMR (150 MHz, $CDCl_3$): δ 14.5 ($CH_3$), 61.1 ($CH_2$), 126.5 (CH), 127.4 (CH), 128.0 (CH), 129.5 (C), 130.2 (CH), 130.7 (CH), 136.9 (C), 141.8 (C), 166.5 (C=O).

IR (KBr): ν ($cm^{-1}$) 2984, 2925, 1716 (C=O), 1708 (C=O), 1279, 1179, 1107.

HR-EI$^+$-MS: $C_{28}H_{26}O_4$ requires 426.1831 amu. found 426.1824 UV-Vis (Solv): (nm) [log ε($M^{-1}$ $cm^{-1}$)] 254 [3.85], 372 [4.74].

Fluorescence ($CH_2Cl_2$): excitation (nm) [emission (nm)] 254 [414, 437], 372 [414, 437]; (cyclohexane) 328 [393, 413].

1,4-Bis[(1E)-2'-(4"-benzoic acid)vinyl]benzene (3)

Using the standard procedure 28 (150.7 mg, 0.35 mmol), LiOH.$H_2O$ (62.3 mg, 1.48 mmol) and 1:9 $H_2O$/EtOH (20 mL) gave an impure dark brown/black precipitate. The crude product was recrystallized from $H_2O$ and EtOH to give acid 3 as a dark brown powder 86.2 mg (66%).

HR-EI$^+$-MS: $C_{24}H_{18}O_4$ requires 370.1205 amu. found 370.1205.

1,4-Bis[2'-(methyl 4"-benzoate)vinyl]benzene (23)

(Methyl 4-carboxybenzyl)triphenylphosphonium bromide (22) (4.43 g, 9.02 mmol) was dissolved in MeOH (100 mL) and treated with NaOMe (45 mL 0.222M in MeOH). The ensuing yellow solution was treated with terephthalaldehyde (512 mg, 3.82 mmol) in one portion and the resultant mixture was heated at reflux for 17 h. The resulting yellow precipitate formed was collected and washed with MeOH to give 23 1.27 g (84%). 40:60 mixture of the E/E and E/Z products.

$^1$H NMR (500.1 MHz, $CDCl_3$): δ 3.834 (s, $CH_3$, EE), 3.837 (s; $CH_3$, EZ), 3.85 (s, $CH_3$, EZ), 6.691 (AB, J=12.3 Hz, vinyl CH, EE), 6.726 (AB, J=12.3 Hz, vinyl CH, EZ), 6.735 (AB, J=12.3 Hz, vinyl CH, EE), 6.774 (AB, J=12.3 Hz, vinyl CH, EZ), 7.10 (s, core ArH, EE), 7.23 (AB, J=8.3 Hz, ArH, EZ), 7.326 (AB, J=16.4 Hz, vinyl CH, EZ), 7.345 (AB, J=8.4 Hz, ArH, EE), 7.389 (AB, J=16.4 Hz, vinyl CH, EZ), 7.393 (AB, J=8.4 Hz, ArH, EZ), 7.54 (AB, J=8.3 Hz, ArH, EZ), 7.72 (AB, J=8.5 Hz, ArH, EZ), 7.84 (AB, J=8.4 Hz, ArH, EE), 7.87 (AB, J=8.4 Hz, ArH, EZ), 7.85 (AB, J=8.5 Hz, ArH, EZ).

$^{13}$C NMR (125.8 MHz, $CDCl_3$): δ 52.1 ($CH_3$), 52.1 ($CH_3$), 126.6 (CH), 126.9 (CH), 127.6 (CH), 128.2 (C), 128.2 (C), 128.3 (C), 128.7 (CH), 128.8 (CH), 129.1 (CH), 129.2 (CH), 129.3 (CH), 129.4 (CH), 129.6 (CH), 130.7 (CH), 131.6 (CH), 135.6 (C), 136.0 (C), 136.1 (C), 141.8 (C), 141.8 (C), 142.0 (C).

IR (KBr): ν ($cm^{-1}$) 3011, 2959, 1716, 1606, 1436, 1276, 1182, 1109.

HR-EI-MS: $C_{26}H_{22}O_4$ requires 398.1518 amu. found 398.1515 amu.

1,4-Bis[2'-(methyl 4"-benzoate)ethyl]benzene (24)

Diester 23 (1.27 g, 3.19 mmol) and Pd/C (10% w/w c.a 100 mg) in 1:1 MeOH/$CH_2Cl_2$ (30 mL) was treated as described in the general procedure section. The crude product was recrystallized from $CH_2Cl_2$ and MeOH to give 1.20 g (93%) as a white solid.

$^1$H NMR (600 MHz, $CDCl_3$): δ 2.93 (AA'BB', 8H, $CH_2CH_2$), 3.91 (s, 6H, $OCH_3$), 7.05 (s, 4H, H2/H3), 7.21 (d, J=7.6 Hz, 4H, H2'), 7.95 (d, J=7.6 Hz, 4H, H3').

$^{13}$C NMR (150 MHz, $CDCl_3$): δ (ppm) 37.2, 38.0, 52.1, 128.1, 128.6, 128.7, 129.8, 139.0, 147.3, 167.3.

IR (KBr): ν ($cm^{-1}$) 2944, 2923, 1726, 1609, 1431, 1280, 1176, 1105.

HR-EI$^+$-MS: $C_{26}H_{26}O_4$ requires 4021831 amu. found 402.1834 amu.

EI$^+$-MS: MI=$C_{26}H_{26}O_4$; m/z: 402.2 (8%)=MI$^+$, 370.1 (33.2%)=[MI-MeOH]$^+$, 253.1 (100%)=[MI-$CH_2C_6H_4CO_2Me$]$^+$, 149.1=[$CH_2C_6H_4CO_2Me$]$^+$.

1,4-Bis[2'-(4"-benzoic acid)ethyl]benzene (25)

Method 1: Diester 24 (308.6 mg, 0.77 mmol), LiOH.H$_2$O (125 mg, 3.0 mmol) in MeOH/H$_2$O (9:1, 20 mL) were treated as described in the general saponification procedure, to provide diacid 25 280 mg (97%).

Method 2: Diacid 3 (107.2 mg, 0.25 mmol) and Pd/C (10% w/w c.a. 10 mg) in 1:1 EtOH/CH$_2$Cl$_2$ (10 mL) was treated as described. The crude mixture containing 29 (103 mg, 96%) was suspended in 9:1 EtOH/H$_2$O (10 mL) and LiOH.H$_2$O (26.3 mg, 0.63 mmol) added and treated under the general saponification procedure described earlier to afford diacid 3 (73.2 mg, 82%)

$^1$H NMR (500.1 MHz, d$_6$-DMSO): δ 2.88 (AA'BB', 8H, CH$_2$CH$_2$), 7.11 (s, 4H, H2/H3), 7.32 (d, J=8.2 Hz, 6H, ArH), 7.85 (d, J=8.2 Hz, 6H, ArH).

$^{13}$C NMR (125.8 MHz, d$_6$-DMSO): δ 36.2, 37.0, 128.3, 128.6, 129.3, 138.7, 146.8, 167.3.

IR (KBr): ν (cm$^{-1}$) 2944, 2923, 1685 (C=O), 1610, 1425, 1318, 1292, 1180, 537.

HR-EI$^+$-MS: C$_{24}$H$_{22}$O$_4$ requires 374.1518 amu.

1,3-Bis[2'-(methyl 4"-benzoate)vinyl]benzene (4)

Isophthaldehyde 30 (460 mg, 3.43 mmol), xx (4.4 g, 8.95 mmol), NaOMe (20 mL, 1.0 M) in MeOH (100 mL) were treated under analogous conditions to those described for the preparation of alkene 23. The white precipitate was filtered, washed with MeOH, and dried to give 4 (0.85 g, 62%). The product was a 44:56 mixture of the E/E and E/Z products.

$^1$H NMR (600.1 MHz, CDCl$_3$): δ 3.82 (s, CH$_3$, ct), 3.83 (s, CH$_3$, E/E), 3.85 (s, CH$_3$, E/Z), 6.64 (AB, J=12.4 Hz, trans vinyl CH, E/E), 6.67 (AB, J=12.4 Hz, trans vinyl CH, E/E), 6.76 (AB, J=12.3 Hz, trans vinyl CH, E/Z), 6.81 (AB, J=12.3 Hz, trans' vinyl CH, E/Z), 7.05 (dd, J$_1$=7.6 Hz, J$_2$=1.4 Hz, H4, ee), 7.08 (s, H2, ee), 7.10 (d, J=7.7 Hz, H4/H6, E/Z) 7.13 (AB, J=16.5 Hz, cis vinyl CH, E/Z), 7.17 (t, J=7.6 Hz, H5, E/E), 7.25 (AB, J=8.2 Hz, H2', E/Z), 7.27 (t, J=7.7 Hz, H5, E/Z), 7.33 (AB, J=16.5 Hz, cis vinyl CH, E/Z), 7.36 (AB, J=8.2 Hz, ArH, E/Z), 7.46 (s, H2, E/Z), 7.50 (d, J=7.7 Hz, H4/H6, E/Z), 7.66 (AB, J=8.3 Hz, ArH, E/Z), 7.76 (AB, J=8.4 Hz, H3', E/E), 7.84 (AB, J=8.3 Hz, ArH, E/Z), 7.92 (AB, J=8.4 Hz, ArH, E/Z).

$^{13}$C NMR (150.9 MHz, CDCl$_3$): δ 52.1 (CH$_3$), 52.1 (CH$_3$), 126.2 (CH), 126.6 (CH), 127.0 (CH), 127.6 (CH), 127.9 (CH), 128.1 (C), 128.2 (C), 128.3 (C), 128.3 (CH), 128.3 (CH), 128.7 (CH), 128.9 (CH), 128.9 (CH), 129.2 (CH), 129.3 (CH), 129.3 (CH), 129.5 (CH), 129.6 (CH), 130.9 (CH), 131.7 (CH), 131.8 (CH), 136.6 (C), 136.8 (C), 136.8 (C), 141.6 (C), 141.9 (C), 165.9 (C), 165.9 (C), 166.0 (C).

IR (KBr): ν (cm$^{-1}$) 1720, 1606, 1435, 1280, 1179, 1109.

HR-EI$^+$-MS: C$_{26}$H$_{22}$O$_4$ requires 398.1518 amu. found 398.1518

1,3-Bis[2'-(methyl 4"-benzoate)ethyl]benzene (31)

The E/Z isomeric mixture 4 (499.3 mg, 1.25 mmol) and Pd/C (10% w/w, c.a.~50 mg) in MeOH/CH$_2$Cl$_2$ (40 mL, 1:1) was treated as described previously. The crude product was recrystallized from CH$_2$Cl$_2$/MeOH to give ester 31 (489.7 mg, 98%) as a white solid.

$^1$H-NMR (600 MHz, CDCl$_3$): δ 2.8-2.96 (AA'BB', 8H, CH$_2$CH$_2$), 3.90 (s, 6H, Me), 6.91 (s, 1H, H2), 6.99 (dd, 2H, J=7.6 and 1.4 Hz, 2H, H4/H6), 7.16-7.25 (cm, 5H, ArH), 7.96 (d, J=8.2 Hz, 4H, H3').

$^{13}$C NMR (150 MHz, CDCl$_3$): δ 37.5, 38.0, 52.1, 126.3, 128.0, 128.5, 128.7, 128.8, 129.8, 141.3, 147.3, 167.2.

IR (KBr): ν (cm$^{-1}$) 1715, 1607 (m), 1438, 1279, 1109.

HR-EI$^+$-MS: C$_{26}$H$_{26}$O$_4$ requires 402.1831 amu. found 402.1840.

1,3-Bis[2'-(4"-benzoic acid)vinyl]benzene (32)

Ester 25 (202.6 mg, 0.50 mmol), LiOH.H$_2$O (92.2 mg, 2.20 mmol) and 9:1 MeOH/H$_2$O (30 mL) were treated as described in the general saponification procedure, giving 175.8 mg (94%) as a white solid.

$^1$H-NMR (500.1 MHz, d$_6$-DMSO): δ 2.87 (AA'BB', 8H, CH$_2$CH$_2$), 6.99-7.05 (m, 3H, ArH) 7.15 (t, J=7.4 Hz, 1H, H5), 7.31 (AB, J=8.4 Hz, 4H, H2'), 7.84 (AB, J=8.4 Hz, 4H, H3'), 12.8 (br s, 2H, CO$_2$H).

13C NMR (125.8 MHz, d$_6$-DMSO): δ 36.5, 37.0, 126.0, 128.1, 128.4, 128.6, 128.6, 129.3, 141.0, 146.9, 167.3.

HR-EI$^+$-MS: C$_{24}$H$_{22}$O$_4$ requires 374.1518 amu. found 374.1523.

EI$^+$-MS: MI=C$_{24}$H$_{22}$O$_4$; m/z: (%)=MI$^+$, 239.0 (100%)=[MI-(CH$_2$(C$_6$H$_4$CO$_2$H)]$^+$: 193.0 (34%)=[MI-(CH$_2$(C$_6$H$_4$CO$_2$H)—CO$_2$H—H$^+$]$^+$.

Example 2

Toxicity of a Compound of Formula C-TSB007 (135B)
(A) Haemolytic Activity

In a preliminary study using disk diffusion methodology, a compound of Formula C (TSB007 also known as "135B") (10 mg/ml) had antibacterial activity mostly against Gram-positive bacteria.

As an indicator of toxicity to human cells, haemolysis experiments on sheep erythrocytes were undertaken with TSB007.

10 mg/ml stock solution of TSB007 was prepared in 100% DMSO. Master stock solutions of TSB007 (10 mg/ml) were made by dissolving 20 mg dehydrated compound in 2 ml 100% DMSO. They were stored in foil-covered glass bottles at −20° C. Master stocks stored in this way retained full antimicrobial activity for a minimum period of 6 weeks (results not shown).

Serial, 10-fold dilutions were performed in PBS to make solutions of 1000, 100, 10 and 1 mg/L of TSB007. In microcentrifuge tubes, 500 μl of each dilution was combined with 480 μl PBS and 20 μl washed sheep erythrocytes (100%) so that the final concentration of erythrocytes was 2% and the final concentrations of compound were 500, 50, 5 and 0.5 mg/L. Dilutions of DMSO without. TSB007 were prepared and tested as above to check for haemolysis due to DMSO. A 100% haemolysis control was prepared with 980 μl water and 20 μl erythrocyte suspension. A negative control was prepared with 980 μl PBS and 20 μl erythrocyte suspension. Dilutions and controls were prepared and tested in duplicate.

Tubes were incubated at 37° C. for 2 h on a rocker then centrifuged at 12 000 g for 5 mins. The OD$_{540}$ of the supernatant was determined using 100 μl volumes transferred to a microtitre tray. % haemolysis was determined by blanking the OD against that of the negative control and presenting the resulting OD as a proportion of the OD of the positive control (blanked with water).

The haemolytic activity of TSB007 was very low (Table 1). No haemolysis was observed for the equivalent tests of DMSO.

TABLE 1

Haemolysis of sheep erythrocytes exposed to 0.5-500 mg/L of compound TSB007

| Concentration of compound (mg/L) | Average (SD) % haemolysis (n = 2) |
|---|---|
| 500 | 5.053 (0.595) |
| 50 | 2.316 (0.099) |
| 5 | 2.175 (0.099) |
| 0.5 | −2.316 (0.695) |

(B) Cytotoxic Activity

L929 cells grown to approximately 80% confluency in HGM-M were washed with Hanks, trypsonised to detach the cells from the flask, then diluted to $10^5$ cells/ml in HGM-M and 200 μl used to inoculate the wells of a 96-well microtitre tray. After incubation for 24 h at 37° C., adherent cells were washed with Hanks and then 100 μl HGM-M was added to the wells. Fresh TSB007 master stock solution (10 mg/ml) was serially 10-fold diluted in HGM-M to make solutions of 1000, 100, 10 and 1 μg/ml of TSB007. To the wells of the microtitre tray, 100 μl of these TSB007 solutions were also added, giving final concentrations of 500, 50, 5 and 0.5 μg/ml of TSB007. The same dilutions of DMSO were prepared and tested to check that cytotoxic activity was not due to the DMSO. A negative control was prepared containing only HGM-M, and a positive control was prepared by adding 100 μl of carboplatin (10 mg/ml; Mayne Pharma Pty Ltd, Australia) to wells containing 100 μl HGM-M. Controls and dilutions of TSB007 and DMSO were prepared in duplicate.

After 24 h shaking at 37° C., cytotoxicity was quantified using the neutral red assay. The cells were washed with Hanks then 200 μl HGM-M and 20 μl Neutral Red (3.3 g/L; Sigma-Aldrich) were added to each well. After 2 h shaking at 37° C., cells were washed twice with PBS then 200 μl of 1% acetic acid in 50% EtOH was added to each well to solubilise the stain. After 15 min shaking at 37° C. the $OD_{690\ nm}$ of the wells was measured and subtracted from the $OD_{540\ nm}$. Results were then blanked against wells to which no cells had been added, and converted to a ratio of the OD of the negative control. Ratios 50.5 indicated a cytostatic effect. Testing was performed on two separate occasions.

At concentrations of 0.5-50 μg/ml, TSB007 was not significantly cytostatic to L929 cells (Table 2). The compound was cytostatic at 500 μg/ml. The concentrations of DMSO present in the different TSB007 dilutions were not significantly cytostatic (average ratios ≥0.515). The controls performed as expected.

TABLE 2

Cytotoxicity of 0.5-500 μg/ml TSB007 to L929 cells

| Concentration of compound (μg/ml) | Average (SD) (n = 2)[a] |
|---|---|
| 500 | 0.384 (0.009) |
| 50 | 0.867 (0.030) |
| 5 | 0.882 (0.021) |
| 0.5 | 0.846 (0.285) |

[a]The ratio of the well's OD compared to the OD of the negative control. Ratios ≤0.5 indicate a cytostatic effect and are highlighted.

(C) Ames Test for Mutagenic Activity

To perform the Ames Test on TSB007, a method based on that published by Zeiger and Mortelmans in Current Protocols in Toxicology (1999; Section 3.1.1-3.1.29) was used, in the absence of a metabolic activation system.

Briefly, single colonies from overnight BA cultures of three commonly used *Salmonella* tester strains, *S. typhimurium* TA98, TA100 and TA1535, were used to inoculate 10 ml of nutrient broth. After incubation for 15-18 h at 37° C. with shaking, the concentration of the culture was appropriate for use in the test ($\sim 1-2 \times 10^9$ cfu/ml).

Glucose minimal agar plates with a volume of 20 ml were dried thoroughly. Molten top agars (2 ml) were prepared, supplemented with biotin and trace histidine, and maintained at 43-48° C. To these, 50 μl of the bacterial broth culture ($\sim 1 \times 10^8$ cells) and 100 μl of test solution (see, below) were added. The molten top agar was then poured directly over the surface of the glucose minimal agar and gently swirled to ensure even distribution of the agar. Once solidified, plates were incubated at 37° C. for 48 h then colony counts were performed. Plates were prepared in duplicate.

Test solutions were prepared as follows and included three concentrations of TSB007, a negative solvent control and a positive control (selected from the recommended positive control chemicals and test concentrations) for each strain. Master stock solution (10 mg/ml) was incorporated directly into molten top agar to test the compound at 1000 μg/plate. Dilutions of the stock were prepared in sterile distilled water to also test 100 μg/plate and 300 μg/plate. DMSO (100%) was incorporated into molten top agar as the negative solvent control. This was equivalent to the highest amount of DMSO incorporated into the molten top agar when testing TSB007. The positive controls used were 4-nitro-o-phenlenediamine at 2.5 μg/plate (for TA98), and sodium azide at 5 μg/plate (for TA100 and TA1535).

Colony counts that were two to three times greater than on the negative solvent control plate indicated a mutagenic effect and were regarded as 'positive'. In these cases, the increase in colonies is usually dose related. A 'positive' result in this test is highly predictive of rodent carcinogenicity.

TSB007 gave a 'negative' result (Table 3). In general, the number of colonies on plates containing TSB007 was not greater than on the negative control plates. The positive control performed as expected. The decrease in colony counts at 1000 μg/plate TSB007 may be due to antimicrobial activity against the tester strains.

TABLE 3

Colony counts of three *S. typhimurium* tester strains exposed to different concentrations of TSB007 under Ames Test conditions

| | Number of colonies | | | | |
|---|---|---|---|---|---|
| Strain | Negative Control | Positive Control | TSB007 100 μg/plate | TSB007 300 μg/plate | TSB007 1000 μg/plate |
| TA98 | 14 | 300 | 13 | 11 | 2 |
| | 12 | 285 | 16 | 11 | 3 |
| TA100 | 113 | 350 | 111 | 110 | 88 |
| | 96 | 360 | 92 | 105 | 89 |
| TA1535 | 28 | 600 | 17 | 16 | 0 |
| | 29 | 600 | 29 | 24 | 0 |

Example 3

Antimicrobial Activity of Formula C
(A) Initial Screening by Disk Diffusion

Studies using disk diffusion methodology showed that the compound of Formula C, ("TSB007") (10 mg/ml) had antibacterial activity against a range of organisms, mostly Gram-positive bacteria.

Briefly, blood agar plate (BA) cultures of the 38 organisms listed in Table 5 were prepared over 24 and 48 h for normal and slow-growing organisms, respectively. Pre-dried (30 mins) Mueller Hinton agar plates (MHA; from PathWest Media) were swabbed with 0.5 McFarland suspensions of the BA cultures in saline (0.85% NaCl) as per CLSI guidelines. Anaerobes were instead inoculated onto pre-reduced BA plates, and *Streptococcus* spp. onto MHA containing 5% sheep blood. Two Whatman 6 mm Antibiotic Assay disks were placed onto each inoculated plate. One disk was impregnated with 20 μl 100% DMSO and the second with 20 μl of 10 mg/ml TSB007 in 100% DMSO. Plates were incubated at 35° C. (with 5% $CO_2$ where mentioned in the Table). Zones were measured after 24 and 48 h.

TSB007 resulted in zones of inhibition of all Gram-positive bacteria tested (Table 5). Zones halved with *S. aureus* strains, and were no longer seen with *S. xylosus*, following extended incubation (24 h vs. 48 h), mostly due to the growth of subpopulations of discrete colonies. No zones of inhibition were seen with *C. albicans* nor with Gram-negative bacteria except *M. catarrhalis*. *Y. enterocolitica* had a negligible zone of inhibition after 24 h that was not seen after 48 h.

Figure 3:
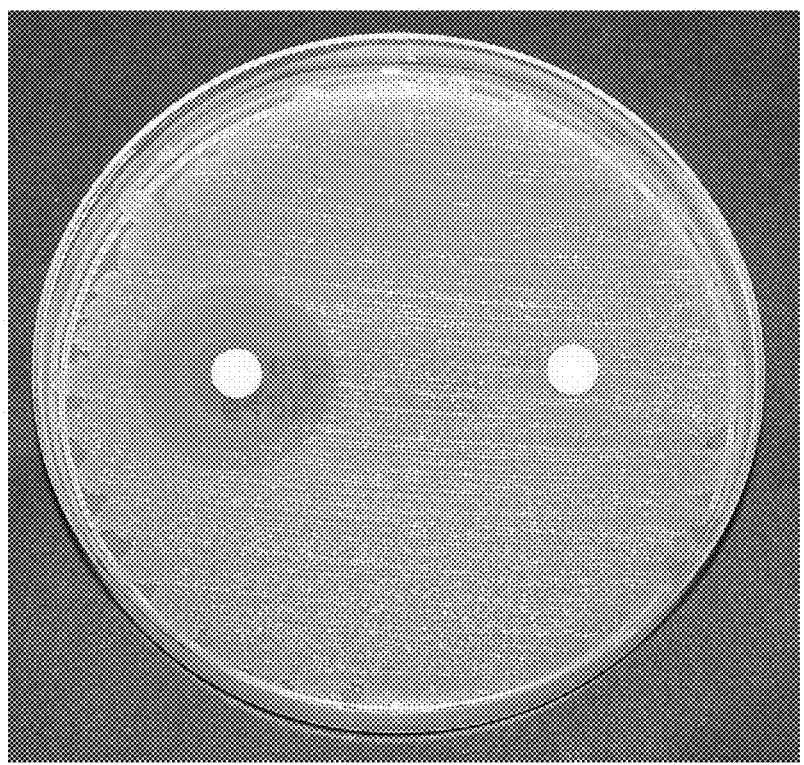
FIG. 3 is a disk diffusion analysis for TSB007 (135B) showing zone inhibition at 48 hours for *Staphylococcus aureus* NCTC 10442 MRSA. The disk on the left contained 20 µl of 10 mg/ml 135B in DMSO and the disk on the right contained 20 µl of DMSO.
Figure 4:
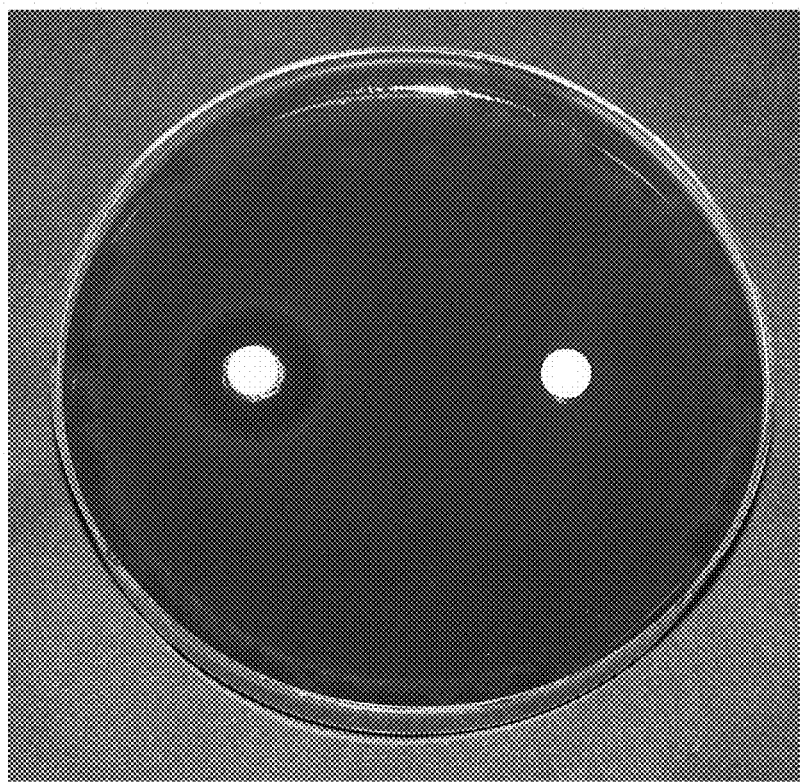
FIG. 4 is a disk diffusion analysis for TSB007 (135B), showing the inhibition at 48 hours for *Streptococcus pneumoniae* ATCC 49619. The disk on the left contained 20 µl of 10 mg/ml 135B in DMSO and the disk on the right contained 20 µl of DMSO.
Figure 5:
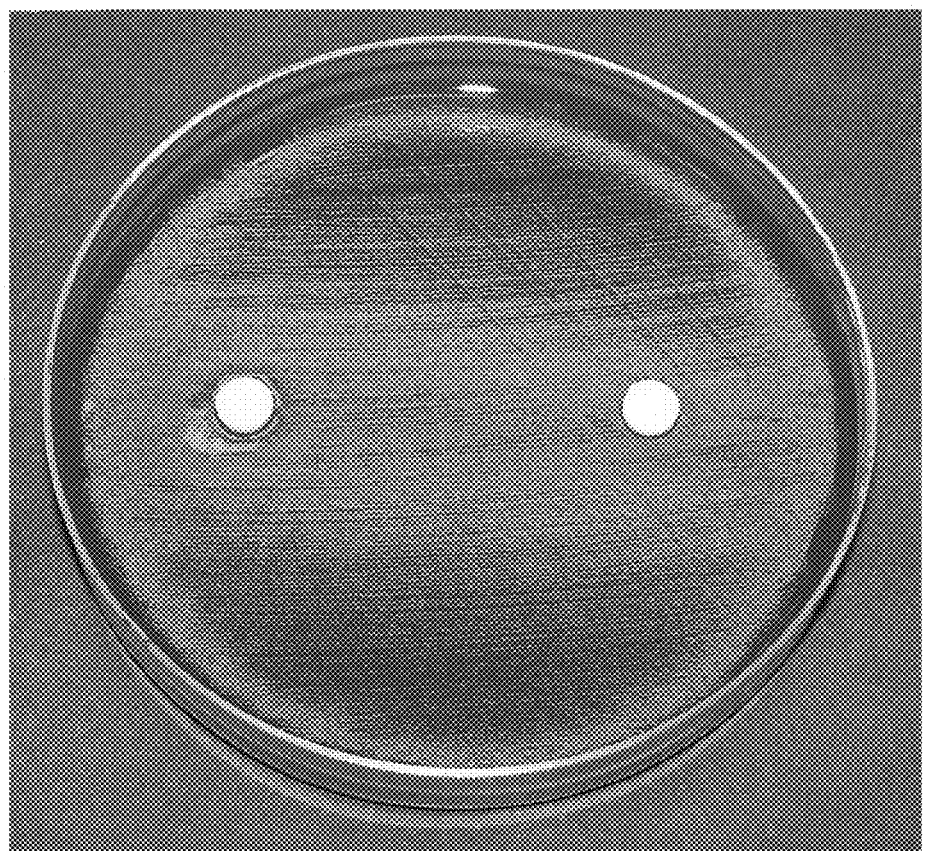
FIG. 5 is a disk diffusion analysis for TSB007 (135B), showing the inhibition at 48 hours for *Clostridium difficile* NCTC 43593. The disk on the left contained 20 µl of 10 mg/ml 1356 in DMSO and the disk on the right contained 20 µl of DMSO.

Photographs were taken after 48 h of all plates where TSB007 produced zones of inhibition. FIGS. 3-5 show a selection of these.

TABLE 5

Disk diffusion zone diameters for compound TSB007 (10 mg/ml, 20 μl) and a DMSO control tested against a panel of Gram-negative bacteria

| Organism | | Special growth conditions? | Zone diameters (trim) | | | | Repeat Results |
|---|---|---|---|---|---|---|---|
| | | | 24 h TSB007 | 48 h TSB007 | 24 h DMSO | 48 h DMSO | |
| Gram-negative | | | | | | | |
| *Acinetobacter baumannii* | ATCC 15308 | No | N/A | N/A | N/A | N/A | N/A |
| *Acinetobacter baumannii* | ATCC 19606 | No | N/A | N/A | N/A | N/A | |
| *Aeromonas hydrophila* | NCTC 8049/ ATCC 7966 | No | N/A | N/A | | | 8 |
| *Burkholderia cepacia* | ATCC 25416 | No | N/A | N/A | N/A | | |
| *Citrobacter freundii* | NCTC 9750/ ATCC 8090 | No | N/A | N/A | N/A | N/A | 9 |
| *Enterobacter cloacae* | NCTC 10005/ ATCC 13047 | No | N/A | N/A | N/A | N/A | |
| *Enterobacter aerogenes* | ATCC 13048 | No | N/A | N/A | N/A | N/A | |
| *Escherichia coli* | NCTC 10538 | No | N/A | N/A | N/A | N/A | 7.5? |
| *Klebsiella edwardsii* | NCTC 10896 | No | N/A | N/A | N/A | N/A | 9 |
| *Klebsiella pneumoniae* | ATCC 13883 | No | N/A | N/A | N/A | N/A | |
| *Moraxella catarrhalis* | ATCC 25238 (instead of NCTC 3625) | Incubated in 5% $CO_2$ | 25 | 25 | N/A | N/A | 36 (NCTC 3625) |
| *Moraxella catarrhalis* | NCTC 3622 | Incubated in 5% $CO_2$ | No growth | | | | |
| *Morganella morganii* | NCTC 235/ ATCC 25830 | No | N/A | N/A | N/A | N/A | |
| *Proteus mirabilis* | NCTC 10975 | No | N/A | N/A | N/A | N/A | 9? |
| *Proteus vulgaris* | NCTC 4635 | No | N/A | N/A | N/A | N/A | |
| *Pseudomonas aeruginosa* | NCTC 10662 | No | N/A | N/A | N/A | N/A | N/A |
| *Salmonella enterica* subsp. *enterica* serovar Typhimurium | ATCC 13311 | No | N/A | N/A | N/A | N/A | 11 |
| *Serratia marcescens* | NCTC 1377 | No | N/A | N/A | N/A | N/A | |
| *Shigella flexneri* | NCTC 8192 | No | N/A | N/A | N/A | N/A | 8.5 |
| *Stenotrophomonas maltophilia* | ATCC 13637 (instead of M2495) | No | N/A | N/A | N/A | N/A | 9 (M2495) |
| *Vibrio cholerae* (non-toxigenic) | M3695 | No | N/A | N/A | 7 | 7 | 7 (other strain?) |
| *Yersinia enterocolitica* | ATCC 9610 (instead of clinical 26609) | No | 7 | N/A | N/A | N/A | 8 (clinical 26609) |

Disk diffusion zone diameters for compound TSB007 (10 mg/ml, 20 μl) and a DMSO control tested against a panel of Gram-positive bacteria and *Candida albicans*

| Organism | | Special growth conditions? | 24 h TSB007 | 48 h TSB007 | 24 h DMSO | 48 h DMSO | Repeat Results |
|---|---|---|---|---|---|---|---|
| Gram-positive | | | | | | | |
| *Bacillus cereus* | ATCC 13061 | No | 10 | 9 | N/A | N/A | 9 |
| *Bacillus subtilis* | ATCC 6633 | No | 8 | 8 | N/A | N/A | N/A |
| *Enterococcus faecalis* | NCTC 775 | No | 10 | 10 | N/A | N/A | 8 |
| *Enterococcus faecium* | ATCC 19434 | No | 11 | 10 | N/A | N/A | |
| *Listeria monocytogenes* | NCTC 7973 | No | 9 | 9 | N/A | N/A | 15? |
| *Micrococcus luteus* | ATCC 10240 | No | 26 | 26 | N/A | N/A | 32 |
| *Staphylococcus aureus* | NCTC 6571/ ATCC 9144 | No | 20 | 9 | N/A | N/A | 21 |
| *Staphylococcus aureus* (methicillin resistant) | NCTC 10442 | No | 18 | 9 | N/A | N/A | 23 |

TABLE 5-continued

| | | | | | | | |
|---|---|---|---|---|---|---|---|
| *Staphylococcus epidermidis* | ATCC 12228 | No | 22 | 22 | N/A | N/A | 20 |
| *Staphylococcus xylosus* | ATCC 29971 | No | 17 | N/A | N/A | N/A | 18 |
| *Streptococcus pneumoniae* | ATCC 49619 | Mueller Hinton + Blood & Incubated in 5% $CO_2$ | 16 | 16 | N/A | N/A | 26 (strain 12213) |
| *Streptococcus pyogenes* | NCTC 8191 | Mueller Hinton + Blood & Incubated in 5% $CO_2$ | 14 | 14 | N/A | N/A | 17 |
| Anaerobes | | | | | | | |
| *Bacteroides fragilis* (Gram-neg) | ATCC 23745 | BA - prereduced | N/A | N/A | N/A | N/A | |
| *Clostridium difficile* (Gram-pos) | NCTC 43593 | BA - prereduced | 10 | 10 | N/A | N/A | |
| *Clostridium perfringens* (Gram-pos) | ATCC 2734 | BA - prereduced | 12 | 12 | N/A | N/A | |
| Yeast | | | | | | | |
| *Candida albicans* | ATCC 24433 (instead of ATCC 10231) | MHA used | N/A | N/A | N/A | N/A | N/A |

Note.
N/A indicates no activity. No result indicates the organism was not tested.

(B) Anaerobic Screening

While the above study showed compound TSB007 to be active against Gram-positive bacteria, the zones of inhibition were smaller for the anaerobic Gram-positives. The Gram-negative anaerobe was not inhibited by TSB007. The compound may therefore be less active in an anaerobic environment. *Staphylococcus aureus* is a facultative anaerobe. The membrane potential is reduced for this organism when grown anaerobically and therefore can affect susceptibility to certain antibiotics.

To confirm the compound was also active against *S. aureus* in an anaerobic environment, zones of inhibition of *S. aureus* grown aerobically and anaerobically were compared.

The method described above was used for this investigation except that two MHA plates were prepared for each organism with one examined after aerobic incubation and the other after anaerobic incubation. The organisms tested included *S. aureus* NCTC 6571, *S. aureus* NCTC 10442, and *S. epidermidis* ATCC 12228. The results are shown in Table 6. Zones of inhibition were larger when these organisms were incubated anaerobically compared to aerobically. This was largely due to a lack, when tested anaerobically, of the "creeping" zones (a zone of faint growth within the main zone of inhibition) seen on plates incubated aerobically. No zones of inhibition were seen for DMSO only.

TABLE 6

Disk diffusion zone diameters for compound TSB007 (10 mg/ml, 20 µl) against *Staphylococcus* spp. incubated aerobically and anaerobically

| | Zone diameters (mm) | | | |
|---|---|---|---|---|
| | 24 h | | 48 h | |
| Organism | $O_2$ | $AnO_2$ | $O_2$ | $AnO_2$ |
| *S. aureus* NCTC 6571 | 14 | 18 | No zone | 18 |
| *S. aureus* NCTC 10442 | 14 | 17 | 11 | 17 |
| *S. epidermidis* ATCC 12228 | 18 | 22 | 18 | 22 |

Example 4

MIC and MBC by Broth Microdilution
(A) MIC and MBC by Broth Microdilution

The method used was based on CLSI protocols for broth microdilution testing of these species. As recommended by CLSI, inocula were prepared by direct colony suspension, and the media used were cation-adjusted Mueller Hinton broth (CA-MHB) for *Staphylococcus* spp. and CA-MHB containing 5% lysed horse blood (CA-MHB+LHB) for *Streptococcus* spp. Briefly, 24 h blood agar plate (BA) cultures of *Staphylococcus aureus* strains NCTC 6571, ATCC 29213, ATCC 33592 (MRSA) and NCTC 10442 (MRSA), *Staphylococcus epidermidis* ATCC 29971, *Staphylococcus* xylosus ATCC 29971, *Streptococcus pneumoniae* strains ATCC 49619 and ATCC 6305, and *Streptococcus pyogenes* strains NCTC 8191 and NCTC 8302 were used to prepare 0.5 McFarland suspensions in saline. Two 640 µg/ml working stocks of TSB007 were prepared from a fresh master stock, one in CA-MHB for testing against the *Staphylococcus* spp. and the other in CA-MHB+LHB for testing against *Streptococcus* spp. The working stocks were further diluted ⅒ in these broths for adding to microtitre trays to test MICs of 32, 16, 8, 4, 2, 1, 0.5, 0.25, 0.125 and 0.06 µg/ml.

The wells of two 96-well microtitre trays (one for *Staphylococcus* spp. and one for *Streptococcus* spp.) were filled with 100 µl of the appropriate broth, except for the first column. The last column, a sterility control containing no TSB007 or inoculum, was filled with an additional 100 µl broth. Then 100 µl of the 64 µg/ml TSB007 solution was added to the first two columns, the contents of column 2 was mixed, then 100 µl of this was used in two-fold serial dilutions along the rest of the tray except the last two columns. The final 100 µl was discarded. The second last column was used as a growth control so did not have TSB007 added. Finally, to the first 11 wells of one row per strain, 100 µl of a $10^{-2}$ dilution (in the appropriate broth) of the 0.5 McFarland suspension was added. The microtitre trays were then incubated at 35° C. for 24 h before the MICs were read visually. Wells were further subcultured (10 µl drop onto BA then incubated at 35° C. for 24 h) and colonies subsequently counted to determine minimum bactericidal concentrations (MBCs). The concentration of the initial inoculum was confirmed on BA by counting colonies from 2×10 µl spots of $10^{-5}$ dilutions of the 0.5 McFarland suspensions. Testing was performed on two separate occasions.

The concentrations of inocula were largely as expected, equating to $1.0 \times 10^5$-$6.0 \times 10^5$ CFU/ml. Slightly lower concentrations were achieved for *S. xylosus* ATCC 29971 (5.0-7.5×$10^4$ CFU/ml) and *S. pneumoniae* ATCC 49619 (2.5-5.0×$10^4$ CFU/ml). TSB007 was more active against *Staphylococcus* spp. (particularly *S. aureus*) than *Streptococcus* spp. This was consistent with disc diffusion results above. *S. aureus* and *S. epidermidis* had the lowest MICs (4 µg/ml). In general, MBCs were significantly higher than MICs.

TABLE 4

MIC and MBC of compound TSB007 tested against *Staphylococcus* spp. and *Streptococcus* spp.[a]

| Organism | Final inoculum (×$10^5$ CFU/ml) | MIC (µg/ml) | MBC (µg/ml) |
| --- | --- | --- | --- |
| *S. aureus* NCTC 6571 | 3.25-3.75 | 2-4 | >32 |
| *S. aureus* ATCC 29213 | 4.50-5.00 | 4 | >32 |
| *S. aureus* ATCC 33592 (MRSA) | 4.75-6.00 | 2-4 | >32 |
| *S. aureus* NCTC 10442 (MRSA) | 2.25-3.25 | 2-4 | >32 |
| *S. epidermidis* ATCC 12228 | 2.00-3.25 | 2-4 | >32 |
| *S. xylosus* ATCC 29971 | 0.50-0.75 | 8-16 | 8-16 |
| *S. pneumoniae* ATCC 49619 | 0.25-0.50 | 32 | >32 |
| *S. pneumoniae* ATCC 6305 | 1.00-2.00 | >32 | >32 |
| *S. pyogenes* NCTC 8191 | 1.00-2.50 | >32 | >32 |
| *S. pyogenes* NCTC 8302 | 1.00-1.50 | >32 | >32 |

[a]Results are from two independent replicates (B) Expansion of Broth Microdilution MIC and MBC Testing Range for *S. aureus* NCTC 6571 and *E. coli* NCTC 10418

The method described above, with some modifications, was used to determine the MIC and MBC for *S. aureus* NCTC 6571 and *E. coli* NCTC 10418. Concentrations of the compound were previously too low to determine the MBC of this *S. aureus* strain. Modifications were the use of Mueller-Hinton broth (MHB) instead of CA-MHB, the preparation of bacterial inoculum by the growth method instead of direct colony suspension, and the use of more concentrated working stocks and test concentrations of TSB007. Hence, overnight 10 ml MHB cultures prepared from BA cultures were used to make the 0.5 McFarland suspensions in MHB, and doubling dilutions of the working stock at 2048 µg/ml TSB007 were made in MHB across the tray to test MICs of 1024 µg/ml to 0.5 µg/ml. Testing was performed on two separate occasions.

Subsequently, an extended range of concentrations of TSB007 was tested for inhibition of *S. aureus* NCTC 6571 and *E. coli* NCTC 10418. The MIC of *S. aureus* NCTC 6571 was 2 µg/ml, confirming the previous MIC result for this strain, and the MBC was 128-256 µg/ml. The MIC and MBC for *E. coli* NCTC 10418 were 512 µg/ml and >1024 µg/ml, respectively.

Example 5

Time-Kill Experiments

An overnight 10 ml MHB culture of *S. aureus* NCTC 6571 was diluted to 0.5 McFarland in MHB then 1 ml was used to inoculate each of four 100 ml flasks prepared as follows:

1) 9.0 ml MHB (control)
2) 9.99 ml MHB plus 9.7 µl of TSB007 working stock at 2048 µg/ml (1.8 µg/ml)
3) 9.98 ml MHB plus 19.5 µl of TSB007 working stock at 2048 µg/ml (3.6 µg/ml)
4) 6.74 ml MHB plus 256 µl of a TSB007 master stock (320 µg/ml). This equated to 3.2% DMSO which did not have any effect on the viability of *S. aureus* NCTC 6571 (data not shown).

The flasks were incubated at 37° C. for 10 min before inoculation. Samples (0.1 ml) were taken immediately after inoculation (time 0) and then at 15, 30, 60, 120 and 240 min. The samples were immediately diluted $10^{-1}$ in 0.01 M phosphate buffered saline at pH 7.0 (PBS). Further 10-fold dilutions in PBS were made down to $10^{-4}$ until the 60 min time point, and then down to $10^{-6}$ for the remaining time points. Viable counts were estimated using 3×20 µl drops from each dilution on MHA which was then incubated at 37° C. overnight before counting. These were normalised against the initial counts from each flask. Testing was performed on three separated occasions.

Figure 6:
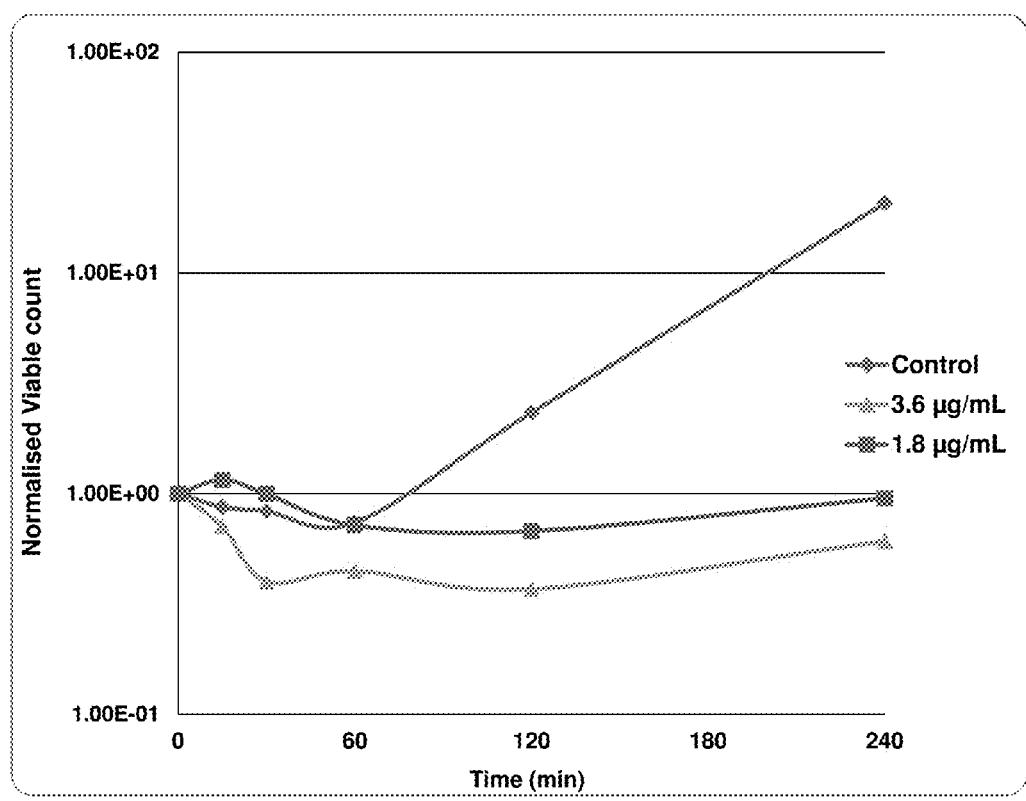
FIG. 6 is a graph of the time-kill experiments of *S. aureus* NCTC 6571 with TSB007 (NAL135B) at concentrations of 1.8 µg/ml and 3.6 µg/ml. Error bars represent standard deviations of triplicate experiments.
Figure 7A:
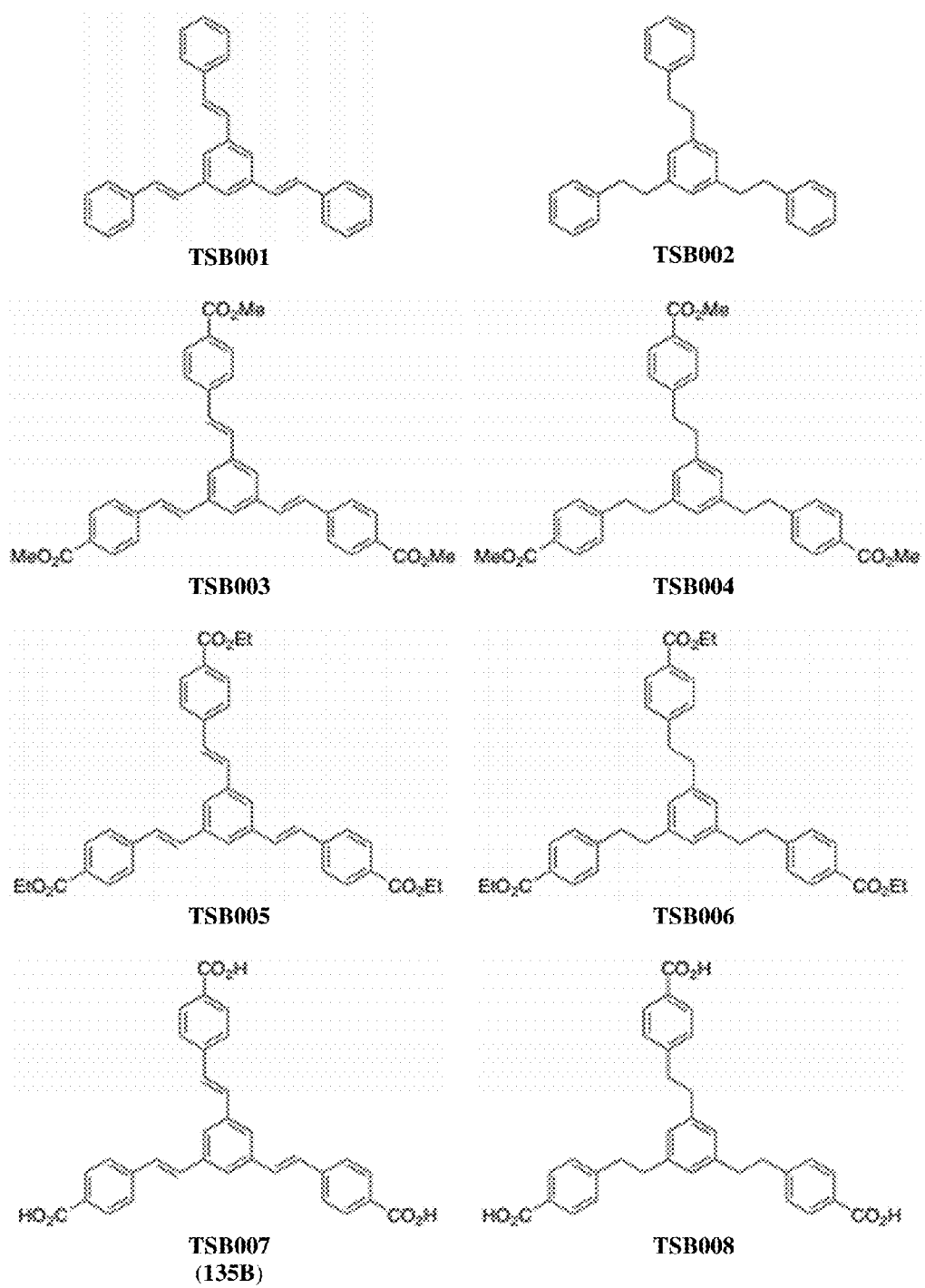
FIG. 7*a-i* shows tristyrylbenzene structural analogues of TSB007.
Figure 7B:
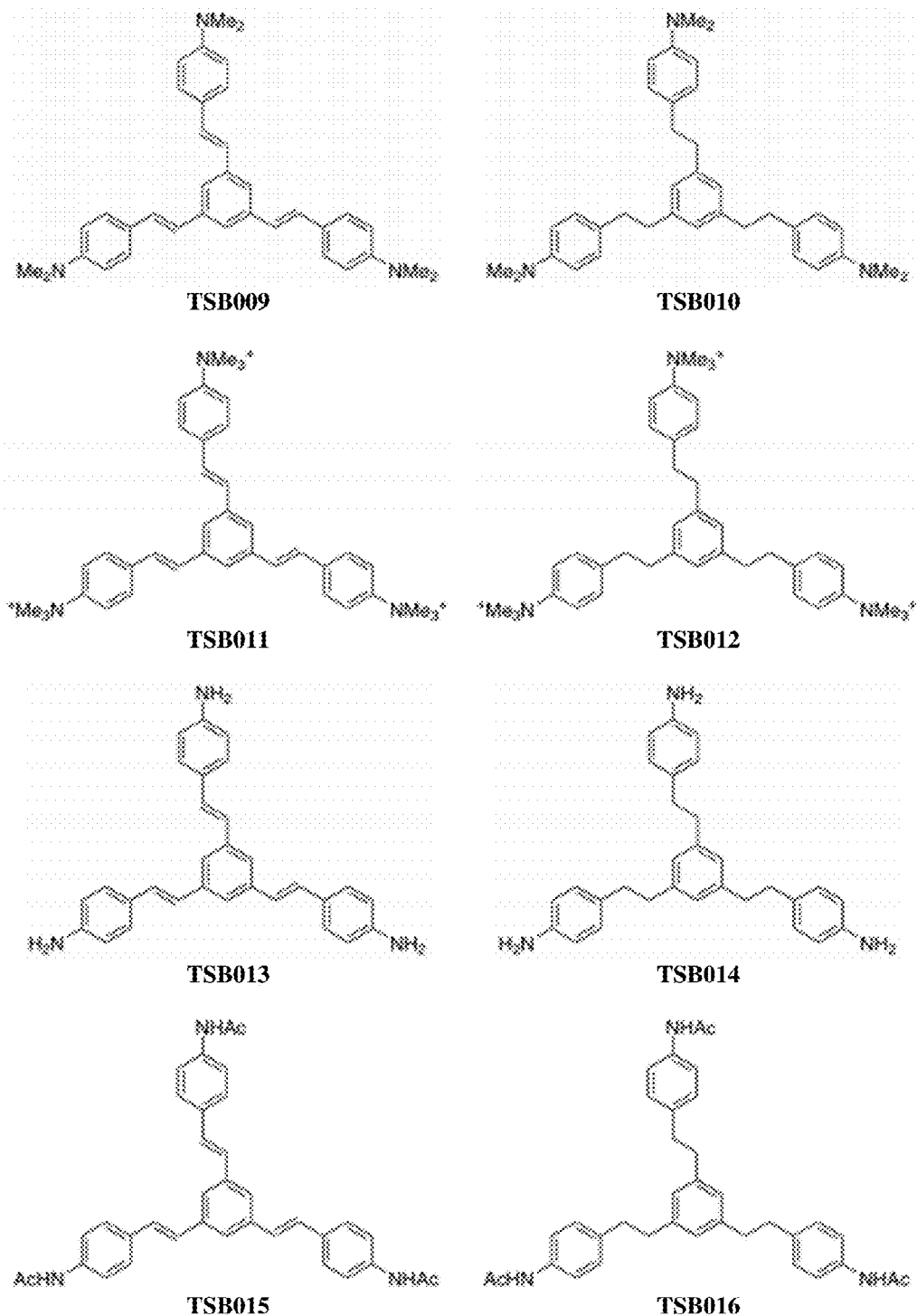
Figure 7C:
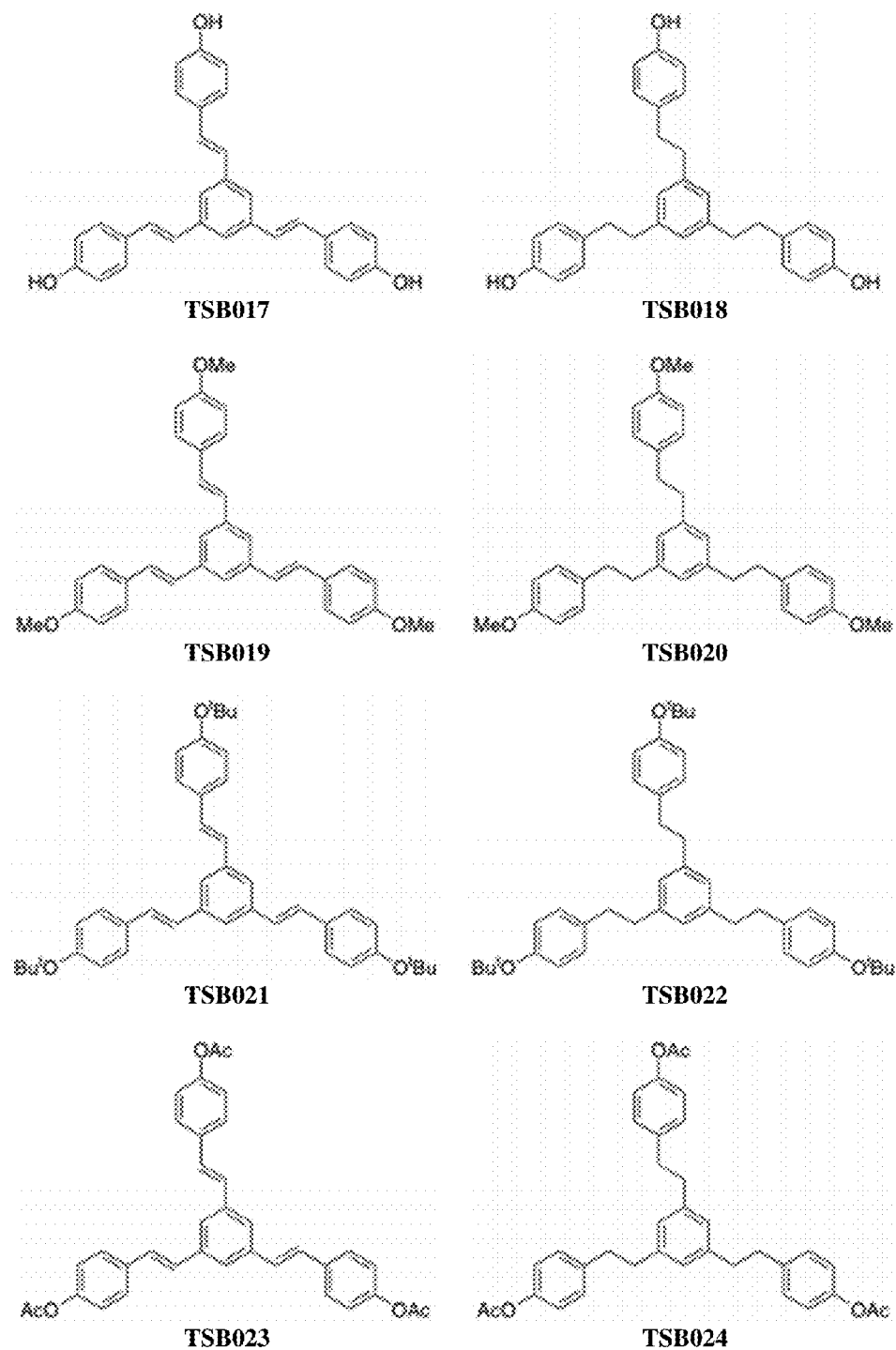
Figure 7D:
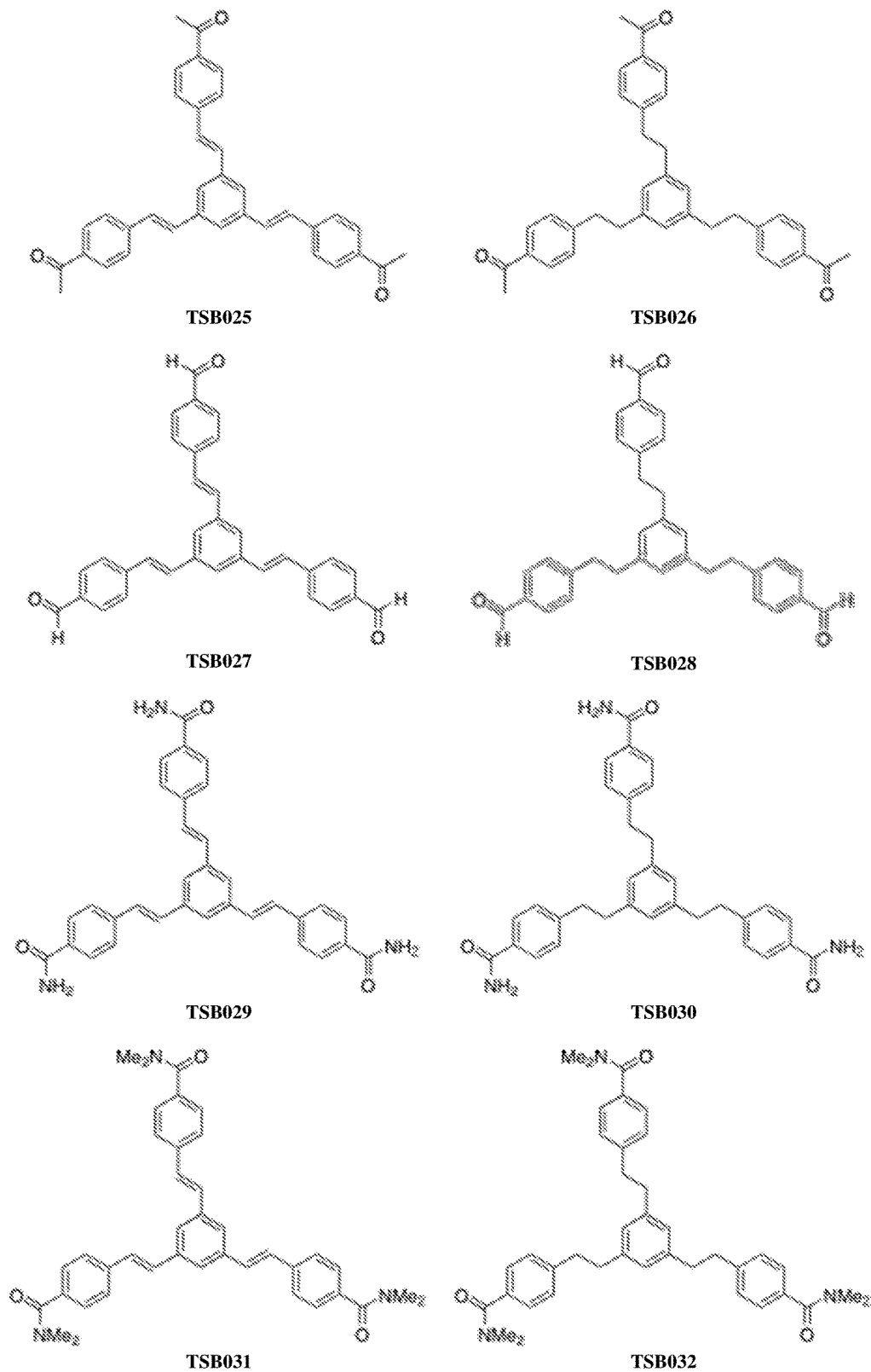
Figure 7E:
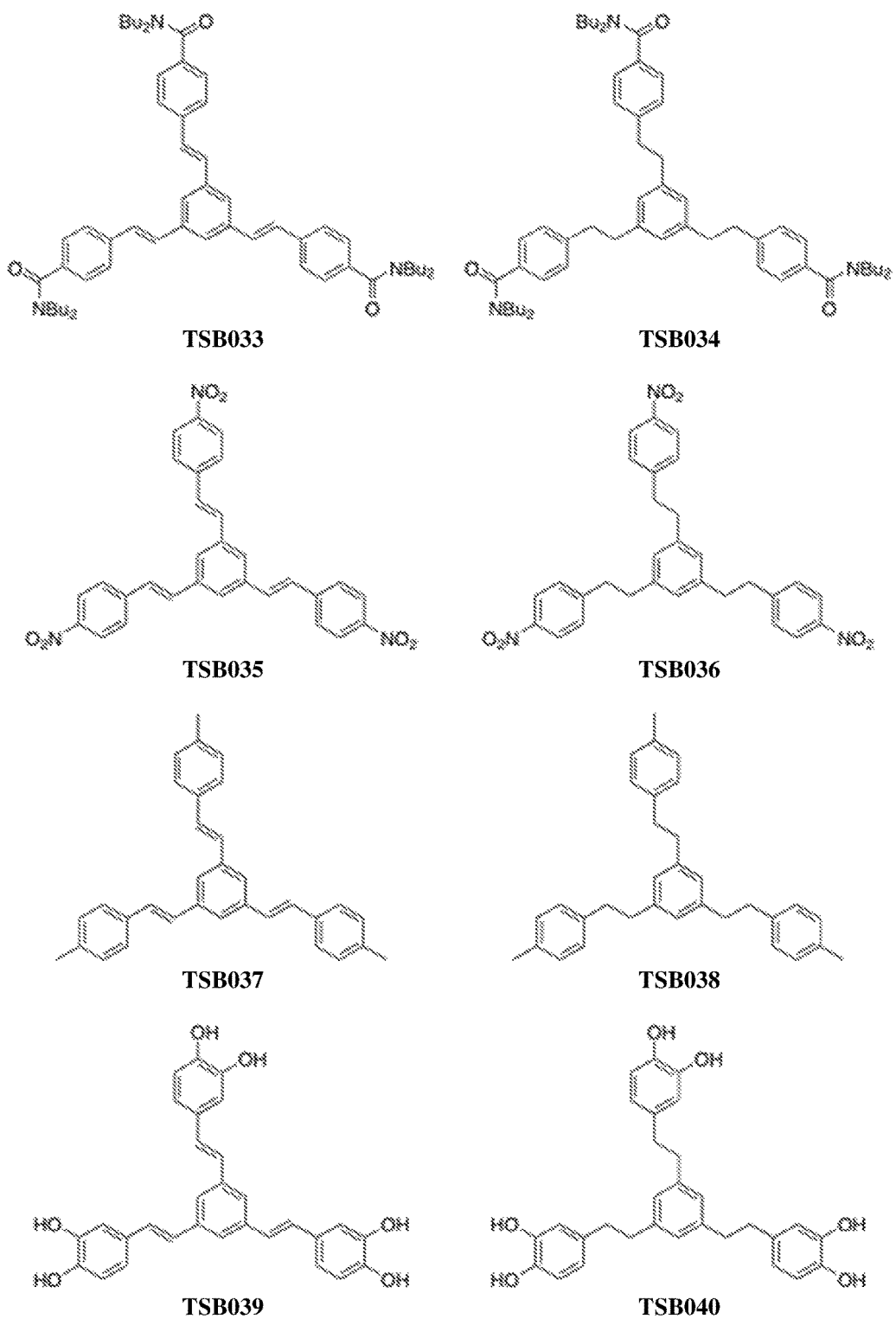
Figure 7F:
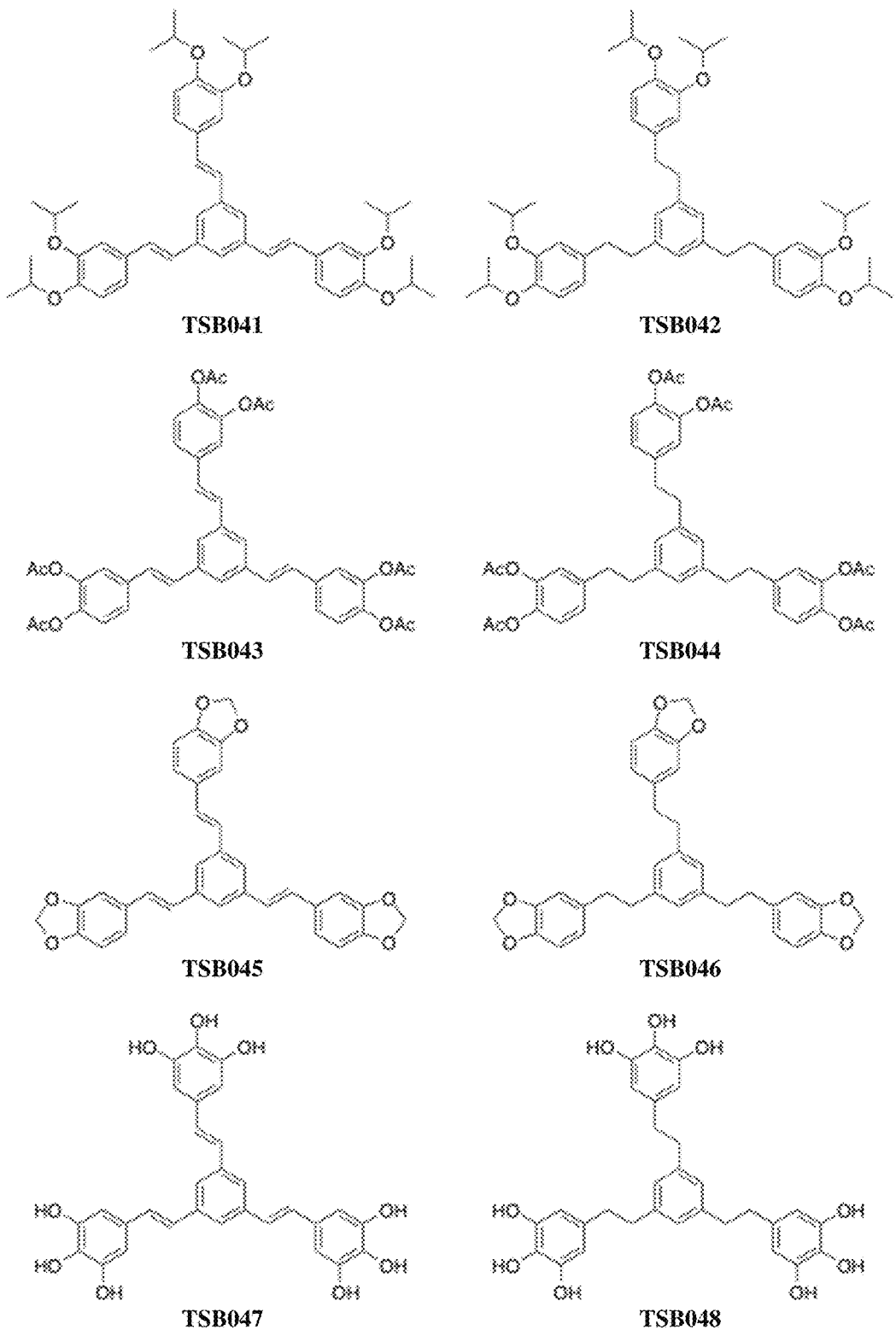
Figure 7G:
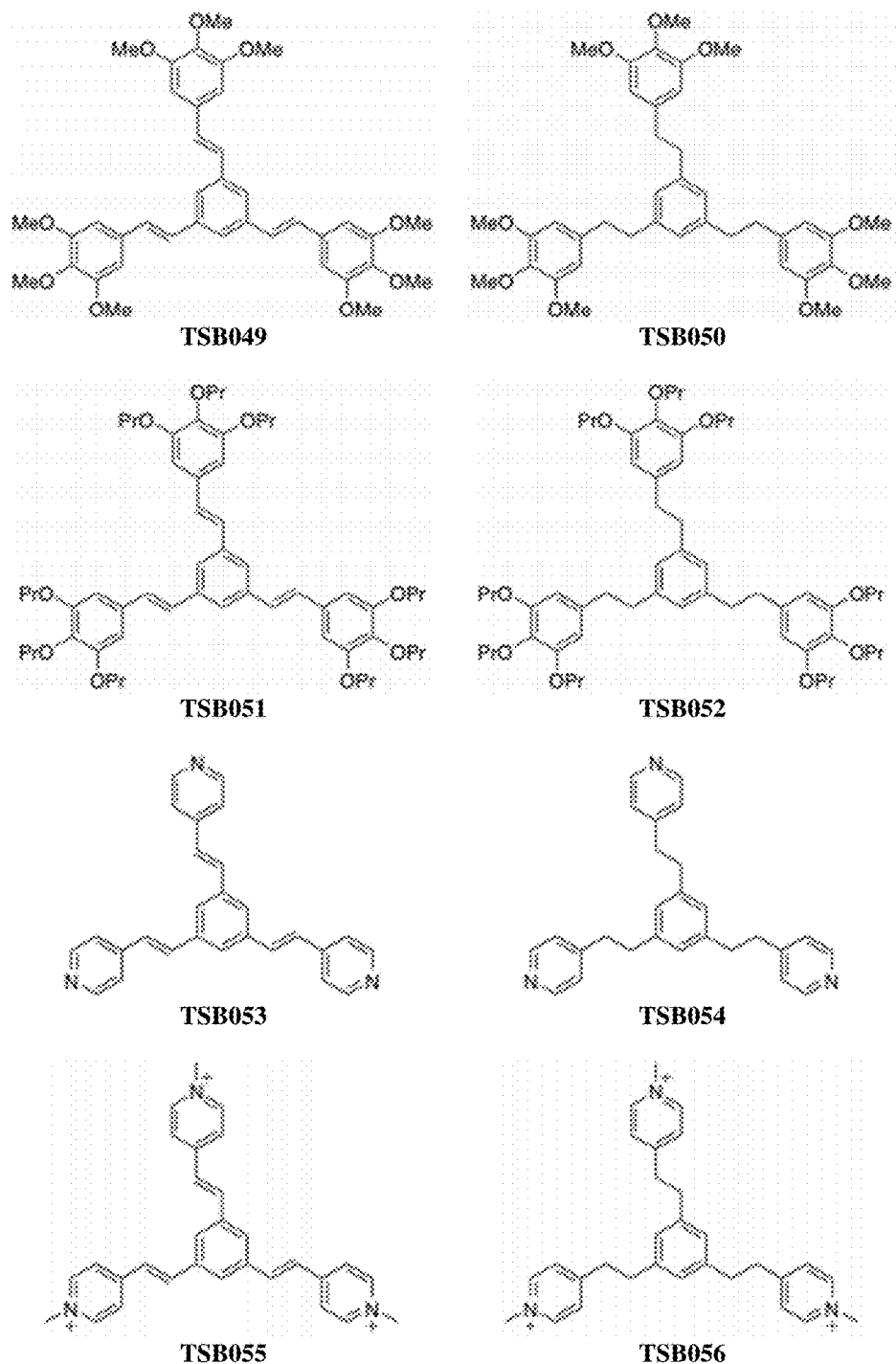
Figure 7G:
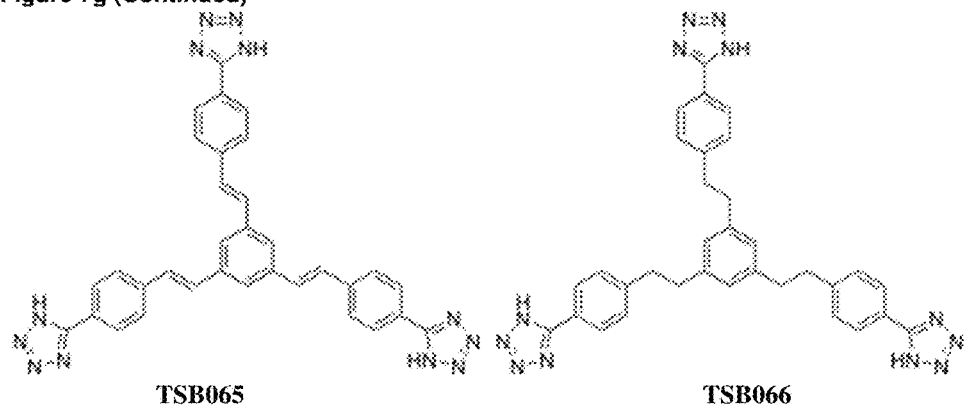
Figure 7I:
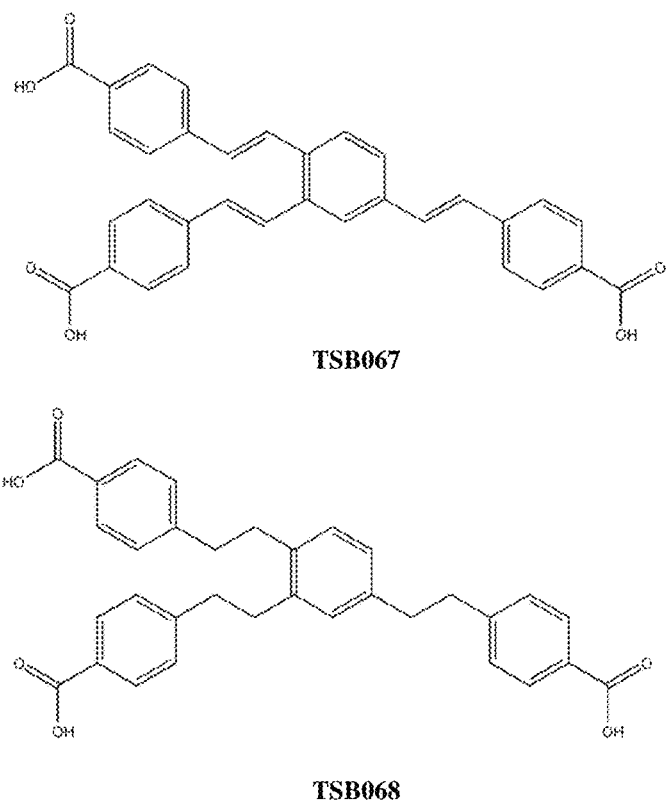
Figure 7H:
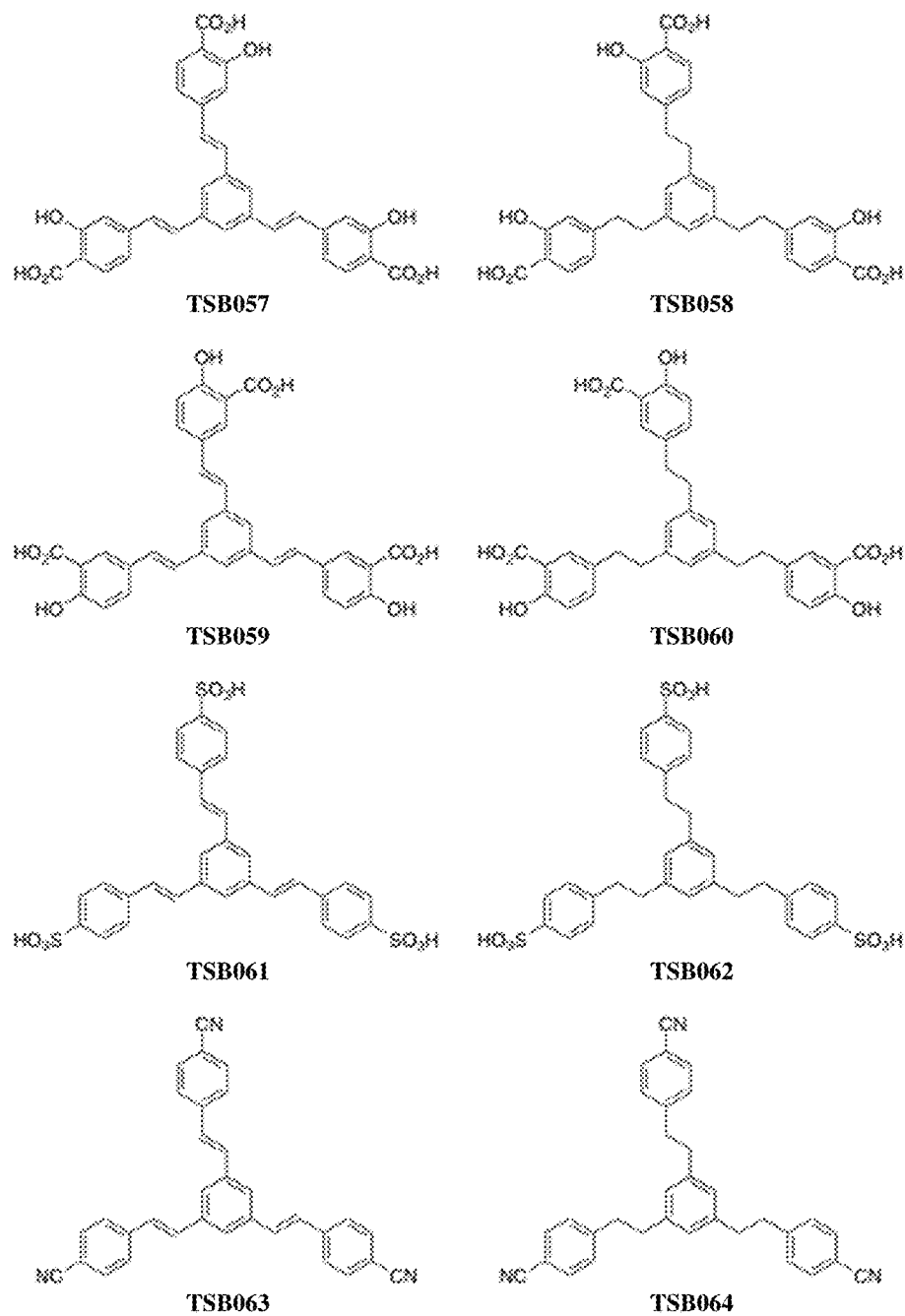
Figure 8:
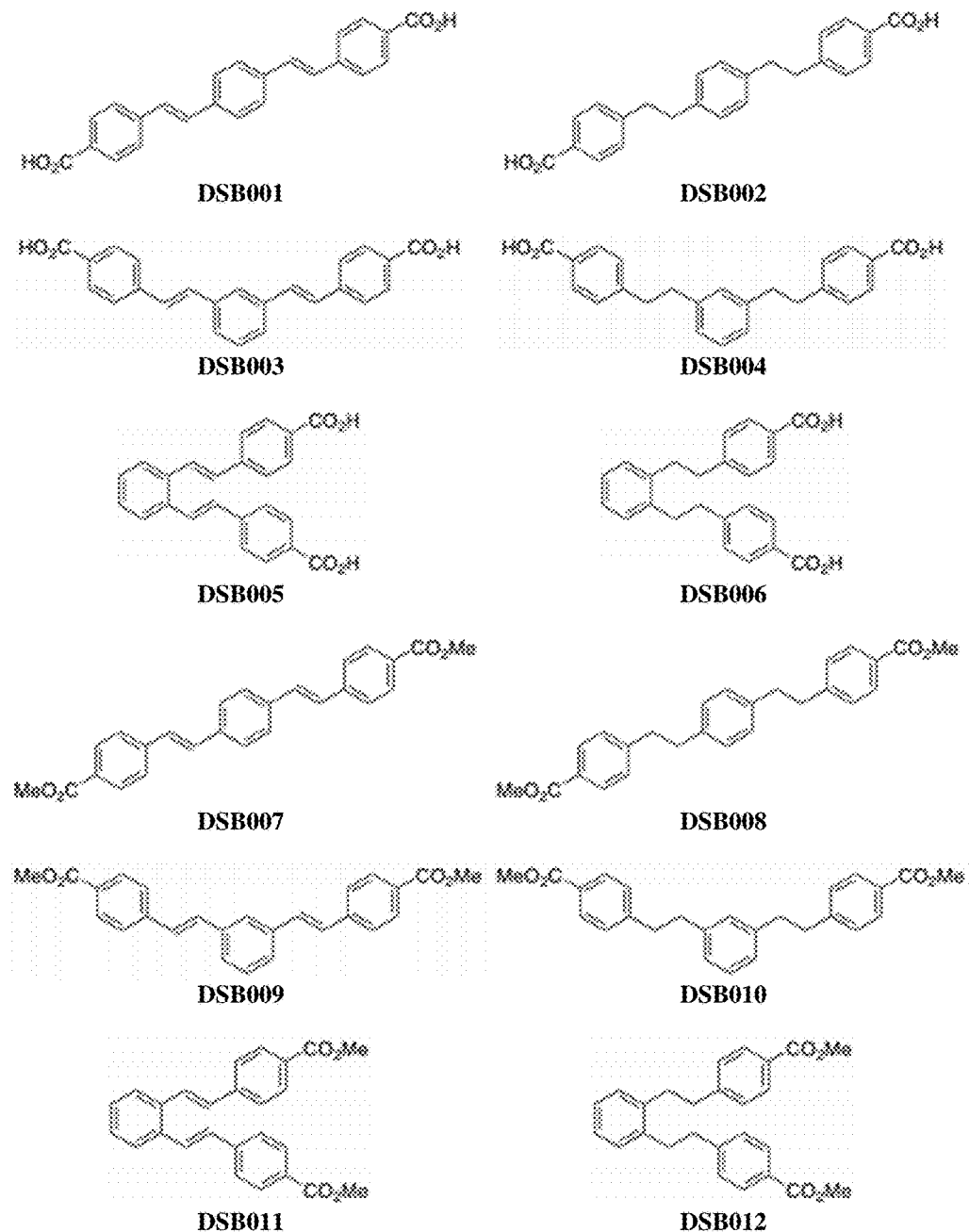
FIG. 8 shows distyrylbenzene structural analogues of TSB007.
Figure 9:
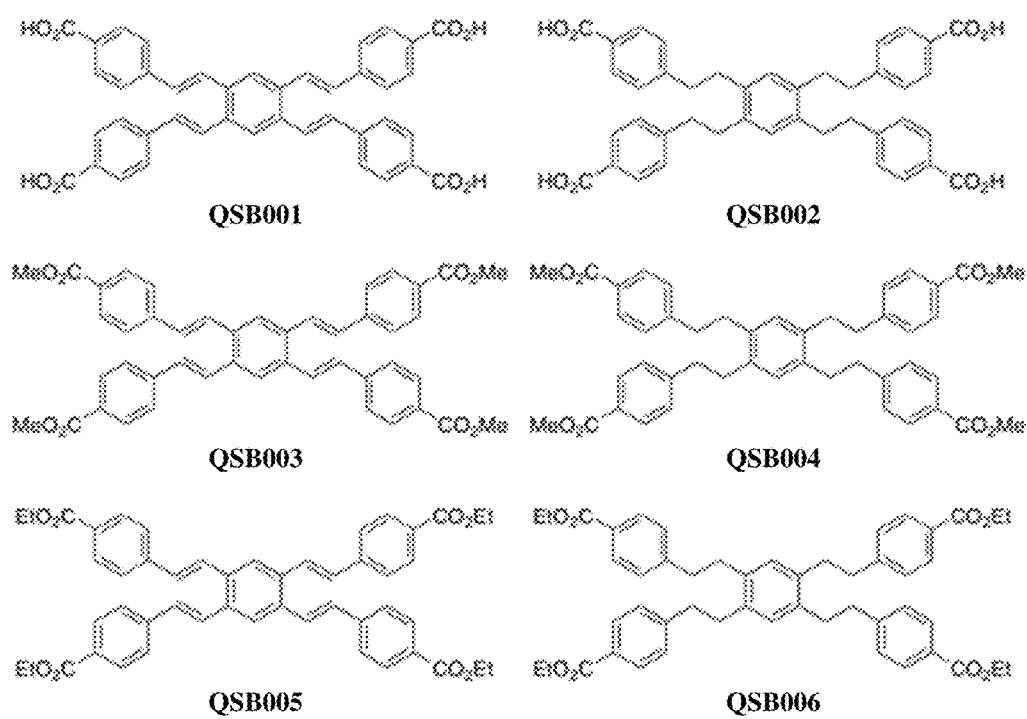
FIG. 9 shows tetrastyrylbenzene structural analogues of TSB007.
Figure 10:
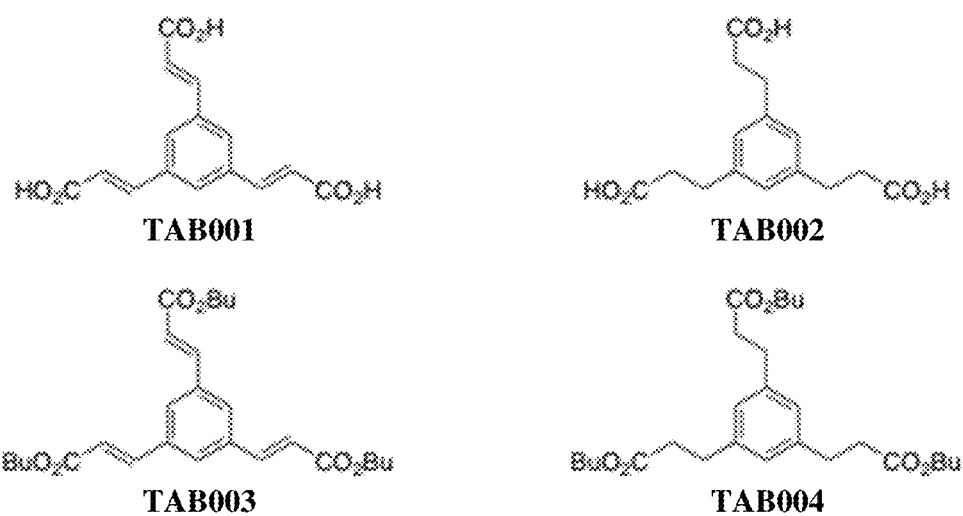
FIG. 10 shows triacryloylbenzene structural analogues of TSB007.
Figure 11:
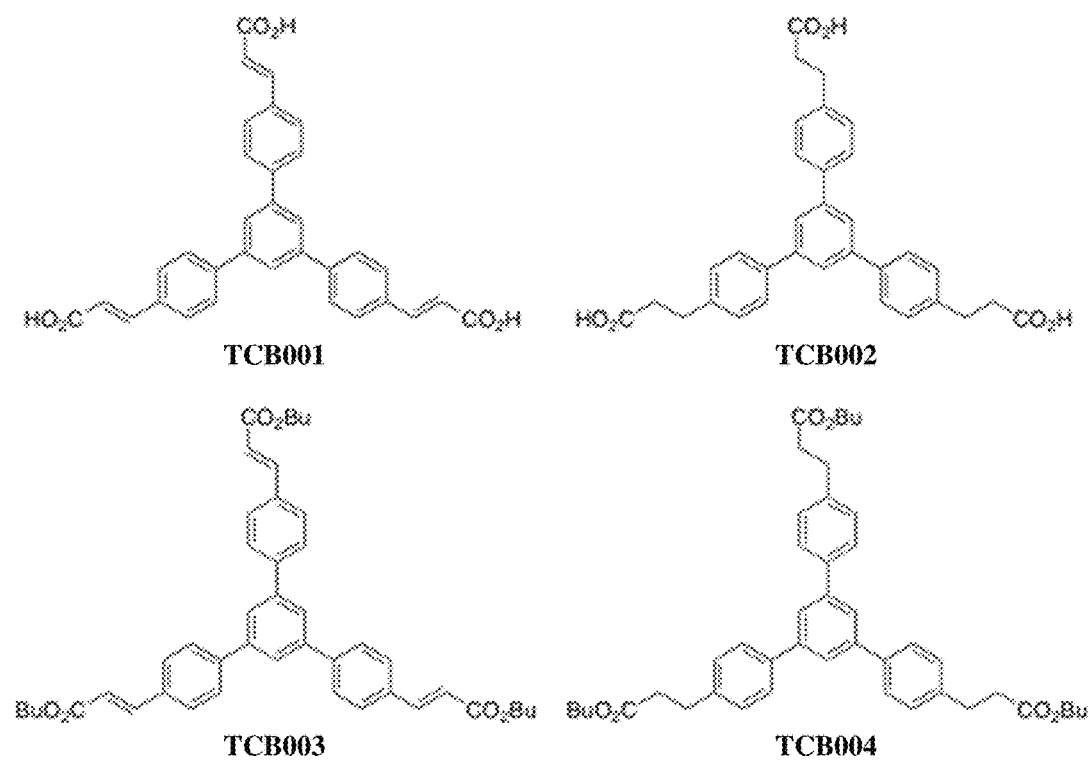
FIG. 11 shows tricinnamylbenzene structural analogues of TSB007.
Figure 12:
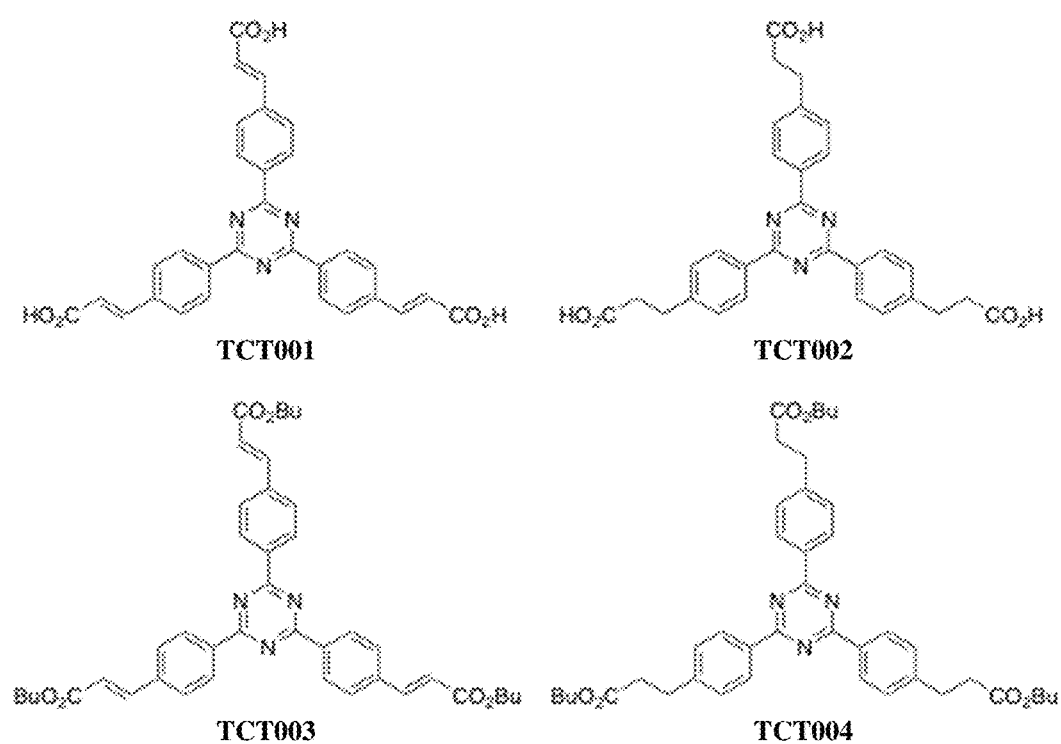
FIG. 12 shows tricinnamyltriazine structural analogues of TSB007.

The viability of *S. aureus* NCTC 6571 cultures containing TSB007 at 1.8 µg/ml (NB. The MIC was 2 µg/ml), 3.6 µg/ml (1.8×MIC) and at 320 µg/ml (1.25×MBC) was tested. The initial concentration of microorganism in each flask was 0.5-1.0×$10^7$ CFU/ml. At both 1.8 µg/ml and 3.6 µg/ml, TSB007 was inhibitory for the 4 h of the experiment (FIG. 6). At 24 h, the cells with TSB007 at 1.8 µg/ml had grown to counts of $10^8$ CFU/ml, and those with 3.6 µg/ml to $10^3$-$10^6$ CFU/ml. The cells with 320 µg/ml at the first time point of 15 min were below the limit of detection with a >99.9% kill.

Example 6

Analogues of TSB007

Various analogues of TSB007 were synthesised and tested in DMSO in disk diffusion assays against *S. aureus* NCTC 6571 using the protocol of Example 3. A number of compounds were also tested against *E. coli* NCTC 10418.

TABLE 5

Compounds tested (see FIGS. 8 to 12 for structure information)

| | Zone of inhibition (mm) | |
| --- | --- | --- |
| Compound | *S. aureus* NCTC 6571 | *E. coli* NCTC 10418 |
| TSB049 | 0 | 0 |
| TSB063 | 0 | 0 |
| TSB037 | 0 | 0 |
| TSB041 | 0 | 0 |
| TSB019 | 0 | 0 |
| TSB023 | 0 | 0 |
| TSB025 | 0 | 0 |
| TSB065 | 14 | 0 |
| TCT003 | 0 | 0 |
| TSB001 | 0 | — |
| TSB009 | 0 | — |
| TSB053 | 0 | — |
| TAB001 | 0 | — |
| TCB001 | 11 | — |
| TCB003 | 0 | — |
| | 0 | — |

— Not tested

Compounds TSB065 and TCB001 were successful at inhibiting growth of *S. aureus* NCTC 6571, with TSB065 giving a zone of inhibition of 14 mm and TCB001 giving a zone of inhibition of 11 mm.

Several analogues were also tested against a range of microorganisms as shown in Table 6.

TABLE 6

Effect of some analogues of TSB007 on growth of various microoganisms.

| Microorganism | Zone of Inhibition (mm) of compounds | | |
|---|---|---|---|
| | TSB068 | TSB067 | QSB001 |
| Gram −ve bacteria | | | |
| A. calcoaceticus ATCC 15308 | 0 | 0 | 0 |
| A. hydrophila NCTC 8049 | 7 | 7 | 7 |
| C. freundii NCTC 9750 | 0 | 0 | 8.5 |
| E. coli NCTC 10418 | 0 | 6.5 | 7 |
| E. coli NCTC 10538 | 0 | 7.5 | 7.5 |
| K. pneumoniae NCTC 10896 | 0 | 0 | 8 |
| M. catarrhalis NCTC 3625 | 32 | 32 | 18 |
| P. mirabilis NCTC 10975 | 0 | 0 | 0 |
| P. aeruginosa NCTC 10662 | 0 | 0 | 0 |
| S. typhimurium ATCC 13311 | 0 | 0 | 8.5 |
| S. flexneri NCTC 8192 | 0 | 0 | 0 |
| S. maltophilia ATCC 13637 | 0 | 0 | 8 |
| V. cholerae non-01 clinical | 0 | 0 | 8 |
| Y. enterocolitica clinical 26609 | 0 | 0 | 7.5 |
| Gram +ve bacteria | | | |
| B. cereus ATCC 13061 | 0 | 0 | 0 |
| B. subtilis ATCC 6633 | 0 | 0 | 0 |
| E. faecalis NCTC 775 | 0 | 0 | 0 |
| L. monocytogenes NCTC 7973 | 15 | 12 | 0 |
| M. luteus ATCC 10240 | 8 | 20 | 0 |
| S. aureus NCTC 6571 | 8 | 14 | 8.5 |
| S. aureus NCTC 10442 | 0 | 12 | 0 |
| S. epidermidis ATCC 1228 | 0 | 11 | 0 |
| S. xylosus ATCC 29971 | 0 | 0 | 0 |
| S. pyogenes NCTC 8191 | 20 | 14 | 8 |
| S. pneumoniae ATCC 49619 | 23 | 16 | 9 |
| Fungi | | | |
| C. albicans ATCC 90028 | 0 | 0 | 0 |

Componds DSB001, DSD002, DSB004, TSB008 and QSB002 showed no zones of inhibition with S aureus NCTC6571 when applied at 10 mg/ml.

The invention claimed is:

1. A compound having a structure selected from the group consisting of:

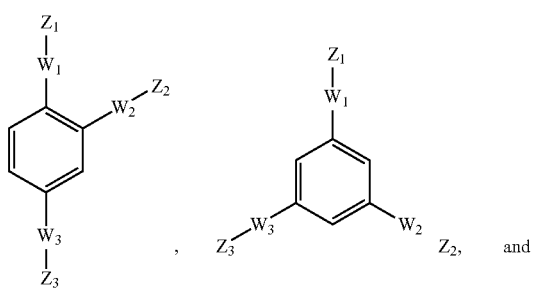

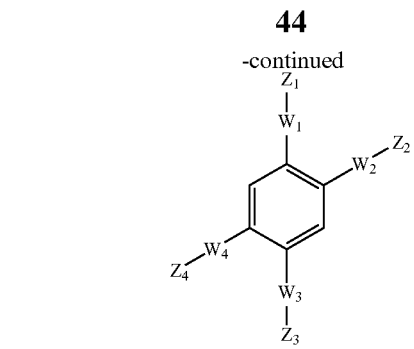

wherein
each of $W_1$, $W_2$, $W_3$, and $W_4$ is the same and is selected from the group consisting of $C_2$ alkyl and $C_2$ alkene;
each of $Z_1$, $Z_2$, $Z_3$, and $Z_4$ is the same and each is:

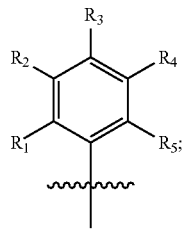

each of $R_1$, $R_2$, $R_4$, and $R_5$ is H;
$R_3$ is —$(CH_2)_n$COOH or an ester thereof and n is 0 or 1;
with the proviso that when the structure is

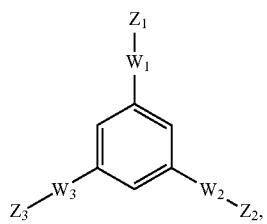

$R_3$ is not —COOCH$_3$,
or a pharmaceutically acceptable salt thereof.

2. The compound of claim 1, wherein each of $W_1$, $W_2$, $W_3$, and $W_4$ is a $C_2$ alkene.

3. The compound of claim 1, having a structure

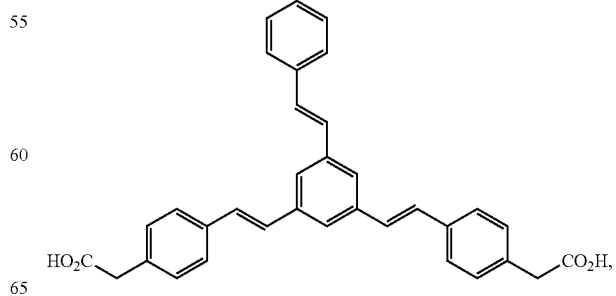

or a pharmaceutically acceptable salt thereof.

4. The compound of claim 1, having a structure

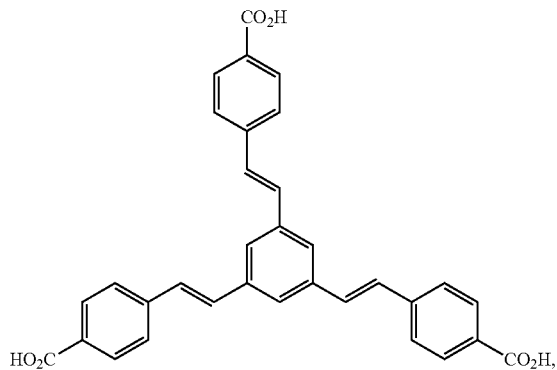 [SMILES: O=C(O)c1ccc(/C=C/c2cc(/C=C/c3ccc(C(=O)O)cc3)cc(/C=C/c3ccc(C(=O)O)cc3)c2)cc1]

or a pharmaceutically acceptable salt thereof.

5. The compound of claim 1, having a structure

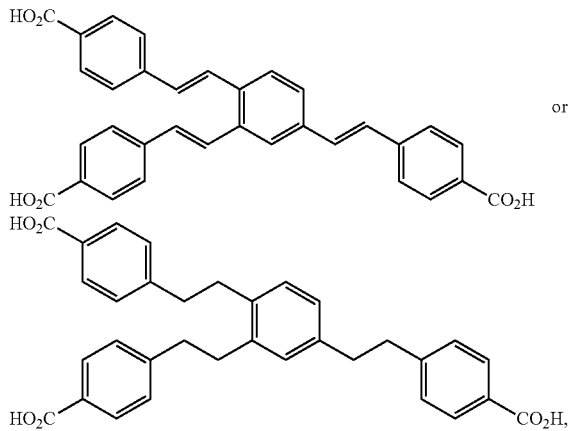

or

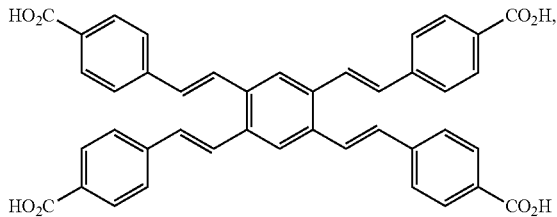 [SMILES: O=C(O)c1ccc(/C=C/c2cc(/C=C/c3ccc(C(=O)O)cc3)c(/C=C/c3ccc(C(=O)O)cc3)cc2/C=C/c2ccc(C(=O)O)cc2)cc1]

or a pharmaceutically acceptable salt thereof.

6. The compound of claim 1, having a structure

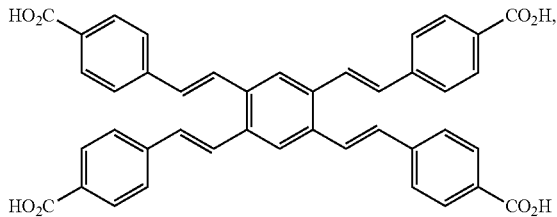 [SMILES: O=C(O)c1ccc(/C=C/c2cc(/C=C/c3ccc(C(=O)O)cc3)c(/C=C/c3ccc(C(=O)O)cc3)cc2/C=C/c2ccc(C(=O)O)cc2)cc1]

or a pharmaceutically acceptable salt thereof.

7. The compound of claim 1, having a structure

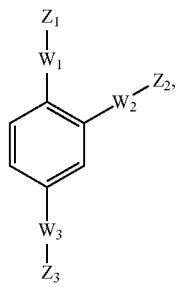

or a pharmaceutically acceptable salt thereof.

8. The compound of claim 7, or a pharmaceutically acceptable salt thereof, wherein $R^3$ is —$(CH_2)_n$COOH or an ester thereof and n is 0 or 1.

9. The compound of claim 7, having a structure

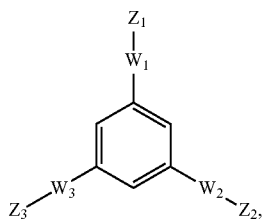

or a pharmaceutically acceptable salt thereof.

10. The compound of claim 9, or a pharmaceutically acceptable salt thereof, wherein $R^3$ is —$(CH_2)_n$COOH or an ester thereof and n is 0 or 1.

11. The compound of claim 1, having a structure

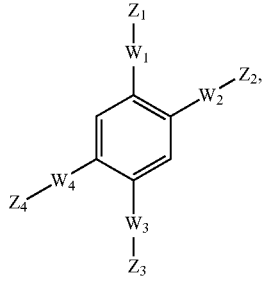

or a pharmaceutically acceptable salt thereof.

12. The compound of claim 11, or a pharmaceutically acceptable salt thereof, wherein $R^3$ is —$(CH_2)_n$COOH or an ester thereof and n is 0 or 1.

* * * * *

UNITED STATES PATENT AND TRADEMARK OFFICE
CERTIFICATE OF CORRECTION

PATENT NO. : 9,738,591 B2
APPLICATION NO. : 14/592629
DATED : August 22, 2017
INVENTOR(S) : Allan James McKinley et al.

It is certified that error appears in the above-identified patent and that said Letters Patent is hereby corrected as shown below:

In the Claims

At Column 46, Line 20, "claim 7," should be -- claim 1, --.

Signed and Sealed this
Fifteenth Day of May, 2018

Andrei Iancu
*Director of the United States Patent and Trademark Office*